(12) United States Patent
Roszkowiak et al.

(10) Patent No.: US 11,013,644 B2
(45) Date of Patent: May 25, 2021

(54) PROTECTIVE UNDERWEAR INCLUDING DISPOSAL ASSEMBLY

(71) Applicant: Medline Industries, Inc., Mundelein, IL (US)

(72) Inventors: Amanda Roszkowiak, Schaumburg, IL (US); Kristy Matus, Grayslake, IL (US)

(73) Assignee: Medline Industries, Inc., Northfield, IL (US)

(*) Notice: Subject to any disclaimer, the term of this patent is extended or adjusted under 35 U.S.C. 154(b) by 324 days.

(21) Appl. No.: 15/980,330

(22) Filed: May 15, 2018

(65) Prior Publication Data
US 2019/0350776 A1 Nov. 21, 2019

(51) Int. Cl.
*A61F 13/15* (2006.01)
*A61F 13/551* (2006.01)
*A61F 13/496* (2006.01)

(52) U.S. Cl.
CPC ........ *A61F 13/5512* (2013.01); *A61F 13/496* (2013.01); *A61F 2013/55125* (2013.01)

(58) Field of Classification Search
CPC ................ A61F 13/5512; A61F 13/496; A61F 2013/55125
USPC .............................. 604/35.13, 385.19, 385.11
See application file for complete search history.

(56) References Cited

U.S. PATENT DOCUMENTS

| | | | |
|---|---|---|---|
| 3,024,788 A | 3/1959 | Lane | |
| 3,093,295 A | 6/1963 | Kugler | |
| 3,114,497 A | 12/1963 | Kugler | |
| 3,196,757 A | 7/1965 | Samways | |
| 3,369,545 A | 2/1968 | Wanberg | |
| 3,585,999 A | 6/1971 | Wanberg | |
| 3,865,110 A | 2/1975 | Traverse | |
| 3,877,432 A | 4/1975 | Gellert | |
| 3,927,674 A | 12/1975 | Schaar | |

(Continued)

FOREIGN PATENT DOCUMENTS

| DE | 3146067 A1 | 7/1982 |
|---|---|---|
| EP | 3178752 A1 | 6/2017 |

(Continued)

OTHER PUBLICATIONS

Notification of Transmittal of the International Search Report and the Written Opinion of the International Searching Authority, or the Declaration; International Patent Application No. PCT/US2019/032379; Medline Industries, Inc.; dated Aug. 20, 2019.

*Primary Examiner* — Jacqueline F Stephens
(74) *Attorney, Agent, or Firm* — Gurr Brande & Spendlove, PLLC.; Robert Dan Spendlove

(57) ABSTRACT

A disposable absorbent article includes a pouch integral to or affixed to an outer layer of the absorbent article. Once soiled with exudates, the pouch is inverted over the absorbent article to conceal and contain the article. The pouch and waist band include integral handles for transporting the exudate soiled article for disposal. The absorbent article may be part of a disposable absorbent article assembly including an individually packaged disposable absorbent article and packaging system, wherein prior to use the absorbent article is sealed within the packaging. The packaging seal is broken to remove the absorbent article and the packaging may be stored for later use or discarded.

19 Claims, 17 Drawing Sheets

(56) References Cited

U.S. PATENT DOCUMENTS

| | | | |
|---|---|---|---|
| 4,034,760 A | 7/1977 | Amirsakis | |
| 4,085,753 A | 4/1978 | Gellert | |
| 4,430,087 A * | 2/1984 | Azpiri | A61F 13/551 |
| | | | 604/385.13 |
| 4,556,146 A | 12/1985 | Swanson et al. | |
| 4,604,096 A * | 8/1986 | Dean | A61F 13/551 |
| | | | 604/385.13 |
| 4,664,663 A | 5/1987 | Brier | |
| 4,674,135 A | 6/1987 | Greene | |
| 4,735,316 A | 4/1988 | Fröidh et al. | |
| 4,743,240 A | 5/1988 | Powell | |
| 4,808,175 A | 2/1989 | Hansen | |
| 4,923,455 A | 5/1990 | Dean et al. | |
| 4,931,052 A | 6/1990 | Feldman | |
| 4,964,859 A | 10/1990 | Feldman | |
| 5,037,414 A * | 8/1991 | Booth | A61F 13/551 |
| | | | 604/385.13 |
| 5,071,414 A | 12/1991 | Elliott | |
| 5,141,505 A | 8/1992 | Barrett | |
| 5,158,386 A | 10/1992 | Lichtwardt et al. | |
| 5,304,158 A | 4/1994 | Webb | |
| 5,575,784 A | 11/1996 | Ames-Ooten et al. | |
| D386,582 S | 11/1997 | Levine | |
| 5,702,379 A | 12/1997 | Preiss | |
| 5,778,110 A | 7/1998 | Furuya | |
| 6,267,232 B1 | 7/2001 | Lejeune | |
| 6,454,748 B1 | 9/2002 | Ives | |
| 6,723,080 B1 | 4/2004 | Habib et al. | |
| 7,347,624 B2 | 3/2008 | Savicki, Sr. et al. | |
| 7,549,538 B2 | 6/2009 | Naoe et al. | |
| D596,287 S | 7/2009 | Tan | |
| 7,569,038 B1 * | 8/2009 | Salem, Jr. | A61F 13/15252 |
| | | | 604/385.01 |
| 7,749,209 B1 | 7/2010 | Vuckovic | |
| 8,029,484 B2 | 10/2011 | Dicarlo | |
| 8,292,863 B2 | 10/2012 | Donoho | |
| 8,905,988 B2 | 12/2014 | Ung et al. | |
| 9,302,823 B2 | 4/2016 | Rudd et al. | |
| 9,315,296 B2 | 4/2016 | Eppelheimer et al. | |
| 9,745,126 B1 | 8/2017 | Cobler | |
| 2002/0004656 A1 | 1/2002 | Khan | |
| 2002/0013566 A1 * | 1/2002 | Chappell | A61F 13/82 |
| | | | 604/385.13 |
| 2002/0029546 A1 | 3/2002 | Gould | |
| 2002/0065500 A1 | 5/2002 | Rossi | |
| 2002/0133134 A1 | 9/2002 | Wilbon | |
| 2002/0165515 A1 | 11/2002 | Burnham | |
| 2004/0134822 A1 | 7/2004 | Otsubo | |
| 2004/0134923 A1 | 7/2004 | Aquino et al. | |
| 2004/0172002 A1 | 9/2004 | Nelson et al. | |
| 2005/0137548 A1 | 6/2005 | Riley | |
| 2005/0182379 A1 | 8/2005 | Olsen et al. | |
| 2005/0228354 A1 | 10/2005 | Scholer | |
| 2005/0256487 A1 | 11/2005 | Williams | |
| 2005/0267432 A1 | 12/2005 | Sundberg et al. | |
| 2006/0020252 A1 | 1/2006 | Strong | |
| 2006/0045391 A1 | 3/2006 | Reglar | |
| 2006/0058770 A1 | 3/2006 | Bohlen et al. | |
| 2006/0100599 A1 | 5/2006 | Engel et al. | |
| 2006/0282056 A1 | 12/2006 | McDonald | |
| 2007/0090009 A1 | 4/2007 | Clare et al. | |
| 2007/0131570 A1 | 6/2007 | Nijs et al. | |
| 2008/0051744 A1 | 2/2008 | Cummings | |
| 2008/0097365 A1 | 4/2008 | Guthrie | |
| 2008/0108965 A1 | 5/2008 | Christensen et al. | |
| 2009/0025339 A1 | 1/2009 | Corlett | |
| 2009/0060397 A1 | 3/2009 | Allegro, Jr. | |
| 2010/0168705 A1 | 7/2010 | Stabelfeldt et al. | |
| 2011/0077610 A1 | 3/2011 | Kikumoto et al. | |
| 2012/0016332 A1 | 1/2012 | Karsenti | |
| 2012/0046631 A1 | 2/2012 | Pardue et al. | |
| 2013/0089278 A1 | 4/2013 | Cobler | |
| 2013/0110072 A1 | 5/2013 | Carvalho et al. | |
| 2013/0123730 A1 | 5/2013 | Corlett | |
| 2013/0126388 A1 | 5/2013 | Hannahan | |
| 2014/0238588 A1 | 8/2014 | Karsenti | |
| 2015/0239589 A1 | 8/2015 | Corlett | |
| 2015/0251816 A1 | 9/2015 | Elkins | |
| 2015/0265476 A1 | 9/2015 | Amiri | |
| 2016/0031610 A1 | 2/2016 | Cobler | |
| 2016/0038352 A1 | 2/2016 | Greene | |
| 2016/0101004 A1 | 4/2016 | Amiri | |
| 2016/0120710 A1 | 5/2016 | Stabelfeldt et al. | |
| 2017/0027773 A1 | 2/2017 | Morgan | |
| 2017/0246057 A1 | 8/2017 | Canales Espinosa De Los Monteros et al. | |

FOREIGN PATENT DOCUMENTS

| | | |
|---|---|---|
| FR | 2699401 A1 | 6/1994 |
| GB | 2414676 A | 7/2005 |
| WO | 2098765 A | 12/2002 |
| WO | 2006073524 A1 | 7/2006 |
| WO | 2009155290 A1 | 12/2009 |
| WO | 2010103516 A1 | 9/2010 |
| WO | 2012118576 A1 | 9/2012 |

* cited by examiner

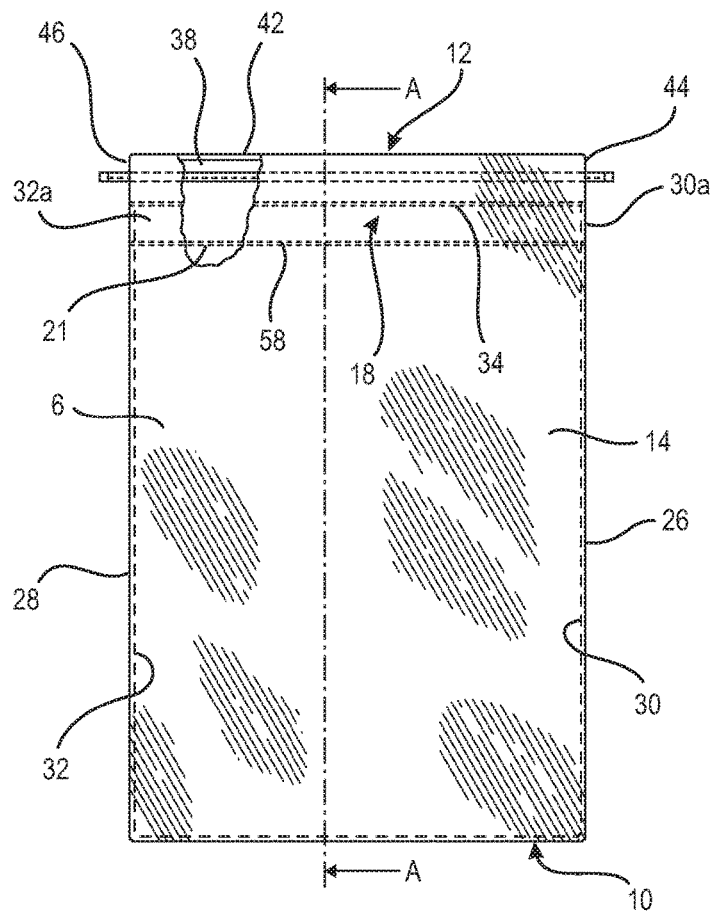
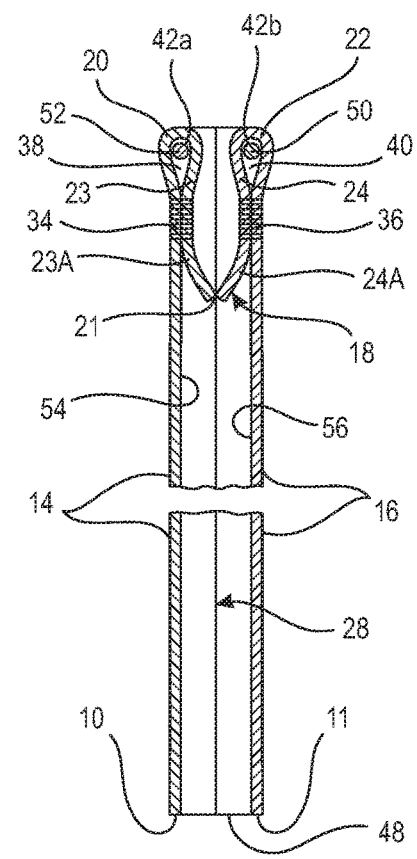
FIG. 3
FIG. 4
Section A-A
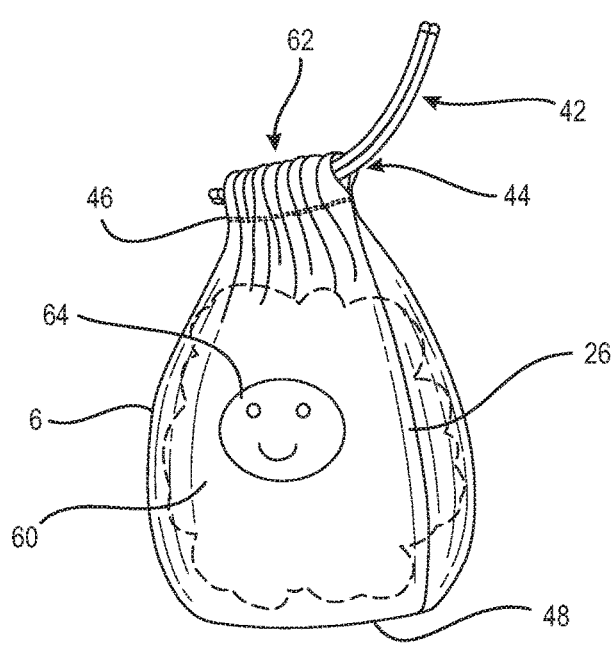
FIG. 5

Section B-B

Section B-B

Section D-D

Detail C

Detail G

Detail E

Section F-F

Detail J

PROTECTIVE UNDERWEAR INCLUDING DISPOSAL ASSEMBLY

FIELD OF THE INVENTION

Embodiments of the present invention relate primarily to absorbent articles such as disposable incontinence articles, namely, disposable underwear and a pouch integral to or affixed to the absorbent article for receiving and concealing a body discharge soiled article. More particularly, embodiments of the invention relate to handles integral or applied to the absorbent article and pouch for transporting a concealed body discharge soiled article, the handles providing a mechanism for avoiding contact with biomatter.

BACKGROUND OF THE INVENTION

Disposable absorbent articles are known in the prior art and have many uses. Whether intended for infants, children, adults or the elderly, disposable pads, napkins, diapers, training pants, briefs, underwear, incontinence articles, hygienic articles and the like are intended to absorb and retain voids, exudate or other body discharges. As used herein, "absorbent article" will refer to all these examples.

Active adults appreciate the freedom afforded to them by incontinence absorbent articles. Such disposable articles can alleviate some of the emotional and physical discomfort of incontinence by absorbing and containing body discharges. Problems arise, however, when bathrooms and public restrooms may not have a readily available garbage can within a stall (for example, men's restroom stalls), or the receptacle (often found among women's restroom stalls) is not sized to receive a bulky, body discharge soiled adult incontinence article. There is a need for transporting used disposable undergarments to and from restrooms/restroom stalls until a suitable trash receptacle can be found. There is also a need for a system to transport absorbent articles soiled with body discharges so that the user's hands do not become contaminated by any biomatter contained therein.

While there are variations in the specific structural features of disposable absorbent articles, they are frequently presented to the consumer in the same manner. Essentially, the disposable absorbent article, irrespective of specific structural features, is packaged in a box, bag or carton with a plurality of disposable absorbent articles from which the consumer withdraws the ready-to-use article as needed. If the consumer needs only one article for later use, the consumer must take precautions to protect the article from becoming soiled or contaminated from the time it is removed from the retail packaging until such time as the article is used.

When traveling or attending to the activities of daily life, bulk packages as described above are indiscreet and impractical. For this reason, individually wrapped absorbent articles have been developed. Furthermore, individually wrapped or packaged absorbent articles are particularly desirable to active adults in the incontinence article retail market.

Individually packaged disposable absorbent articles of the prior art may include a wrapper which overlays only one major surface of the disposable absorbent article and by folding the article and the wrapper as a unit, the wrapper may be sealed thereby providing an individually packaged disposable absorbent article. In use, the wrapper is removed and discarded and is unintended for later use.

In other examples, an individual absorbent article is folded and placed into a sealed pouch to protect the article prior to use. Such pouches are inappropriate for use as a collection bag for a soiled article because disposable absorbent articles will change their shape and become wet and clumsy after having absorbed body discharges, making it difficult to impossible to tuck a used article down into the packaging and/or service bag of the prior art.

In other examples, an individual absorbent article is folded and vacuum sealed within a pouch, pocket, wrapper or bag to reduce the bulk of the unused article. In use, the vacuum seal is broken and the article is removed from the packaging. Again, because soiled articles change their shape after having absorbed body discharges, it is difficult to impossible to insert a soiled article into the packaging and/or service bag of the prior art.

Disposal systems for absorbent articles have been developed which teach disposable bags integrally formed with or applied to an outside surface of the article or placed within/adjacent to an absorbent layer of the article. In use, the disposal bag is either deployed or removed from the absorbent article. The bag is then opened and either inverted over the soiled article or the article is inserted into the bag.

In some examples, the absorbent article must be rolled in onto itself before insertion into the disposal bag. In other examples, the disposal bag may not include a closure system. In still other examples, the bag may include a closure mechanism such as ties, adhesives, hook and loop closures, tongue and groove "zip" closures or other mechanical closure systems. Such closure systems required dexterity to manipulate or may become soiled and thus are not sealable. Further, owing to the awkward shape of an absorbent article after it has become soiled by body discharges, it may be difficult to realign the closure system to completely enclose the soiled article within the disposal bag.

A disadvantage of known packaging, whether for bulk products or individually packaged/wrapped absorbent articles can be found among the packaging itself. Such packaging often includes indicia, logos, designs, bold colors, words and/or phrases which do not offer the user the opportunity to discreetly carry an unused article or transport a soiled article for disposal. That is, the packaging announces what is contained therein.

In other prior art examples, the packaging for an individual article is constructed from a material that produces noise when opening, which in a public restroom setting can cause embarrassment to a user. Where the prior art structure conceals a disposal bag, the disposable absorbent article may change its shape and become wet and clumsy after having absorbed body discharges. Owing to the awkward shape of body discharge soiled absorbent article, it may be difficult to insert and enclose the soiled article within the disposal bag.

Further drawbacks of the prior art include the need for the user to fold and/or roll the soiled article into a compact shape, the process may bring the biomatter contained within the absorbent article into direct contact with the hands of the person handling the article. This process can be both unpleasant and unsanitary.

Embodiments of the present invention are directed to disposable absorbent articles including a pouch for containing a used absorbent article and handles integral to the absorbent article for transport of pouch assembly to an appropriate trash receptacle.

BRIEF DESCRIPTION OF THE DRAWINGS

The various aspects, features and advantages of the disclosure will become more fully apparent to those having ordinary skill in the art upon careful consideration of the following Detailed Description thereof with the accompanying drawings described below.

FIG. 3 is plan view of the unfilled packaging unit of FIG. 2.

FIG. 4 is a cross-sectional view along the line A-A of an unused individually packaged absorbent article.

FIG. 5 is a perspective view of a soiled absorbent article contained within the packaging unit of FIG. 3 and ready for disposal.

Figure 1:
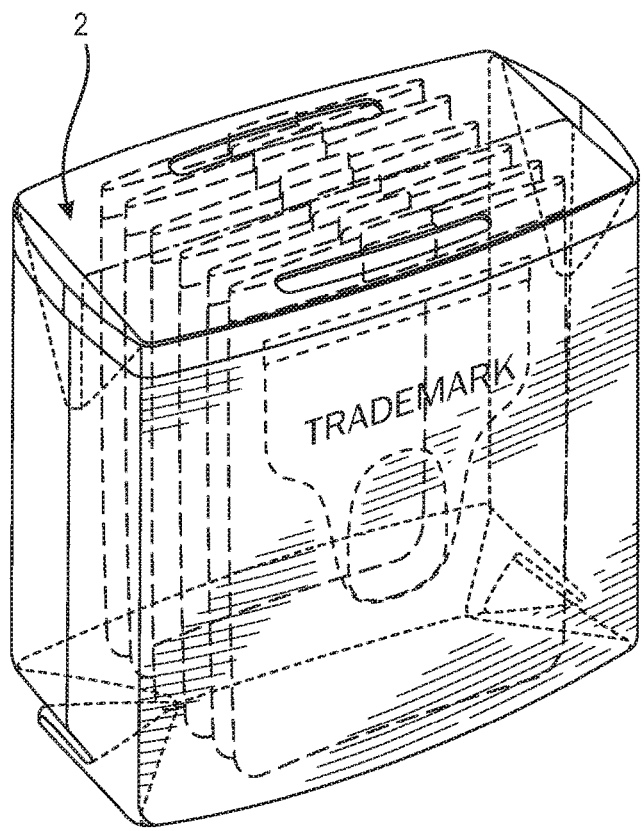
FIG. 1 is a perspective view of retail packaging for a plurality of individually packaged absorbent articles.

While embodiments of the invention are susceptible to various modifications and alternative forms, specific embodiments have been shown by way of example in the drawings and will be described in detail herein. It should be understood however, that the invention is not intended to be limited to the particular forms disclosed. Rather, the invention will cover all modifications, equivalents, and alternatives falling within the spirit and scope of the invention.

DETAILED DESCRIPTION

Embodiments of the invention are now described in detail. Referring to the drawings, like numbers indicate like parts throughout the views. As used in the description herein and throughout the claims, the following terms take the meanings explicitly associated herein, unless the context clearly indicates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions.

As used herein, the following terms have the following meanings:

"Attach" and its derivatives refer to the joining, adhering, connecting, bonding, sewing together, or the like, of two elements. Two elements will be considered to be attached together when they are integral with one another or attached directly to one another or indirectly to one another, such as when each is directly attached to intermediate elements. "Attach" and its derivatives include permanent, releasable, or refastenable attachment. In addition, the attachment can be completed either during the manufacturing process or by the end user.

"Bond" and its derivatives refer to the joining, adhering, connecting, attaching, sewing together, or the like, of two elements. Two elements will be considered to be bonded together when they are bonded directly to one another or indirectly to one another, such as when each is directly bonded to intermediate elements. "Bond" and its derivatives include permanent, releasable, or refastenable bonding.

"Connect" and its derivatives refer to the joining, adhering, bonding, attaching, sewing together, or the like, of two elements. Two elements will be considered to be connected together when they are connected directly to one another or indirectly to one another, such as when each is directly connected to intermediate elements. "Connect" and its derivatives include permanent, releasable, or refastenable connection. In addition, the connecting can be completed either during the manufacturing process or by the end user.

"Integral" is used to refer to various portions of a single unitary element rather than separate structures bonded to or placed with or placed near one another.

"Extensible" refers to materials which elongate or increase in at least one dimension when subject to an external pulling force.

"Elastomeric" refers to a material or composite which can be elongated by a percent of its relaxed length and which will recover, upon release of the applied force by a percent of its elongation. In certain embodiments, an elastomeric material or composite may be capable of being elongated by at least 100 percent, in further embodiments by at least 300 percent of its relaxed length. Embodiments of the elastic material or composite may recover, upon release of an applied force, at least 50 percent of its elongation.

These terms may be defined with additional language elsewhere in the specification.

Absorbent articles as described herein generally include a moisture-pervious inner layer, an absorbent layer, and a moisture-impervious outer layer. Although the remainder of the description will be specifically directed to adult incontinence articles, including disposable briefs and underwear (whether intended for men or women), it is understood that the embodiments may also be implemented on other absorbent articles, whether intended for infants, children, adults or the elderly. As would be understood by one of ordinary skill in the art, such non-limiting examples include: disposable pads, napkins, diapers, training pants, and the like which are intended to absorb and retain body discharges.

It should be observed that the embodiments reside primarily in the combinations of assembly components and method steps for disposal of absorbent articles. Accordingly, the assembly components and the method steps have been represented (where appropriate) by conventional symbols in the drawings, showing only those specific details that are pertinent to understanding the embodiments of the present invention so as not to obscure the disclosure with details that will be readily apparent to those of ordinary skill in the art having the benefit of the description herein.

Referring first to FIG. 1, in a retail setting, disposable absorbent articles are typically sold in multiples. In some instances the absorbent articles are ready for immediate use. In other instances, as disclosed in embodiments of the present application, the absorbent articles are individually wrapped so that they may be transported for later use without fear of the article becoming soiled or contaminated prior to use. Retail packaging 2 may be in the form of a box, bag, carton or other receptacle for holding and displaying a plurality of absorbent articles as is known in the art. Retail packaging 2 is often bulky and discloses the contents of the packaging through the use of indicia, logos, designs, bold colors, words and/or phrases. Such indicia can include sizing, gender and absorbency information, etc.

In accordance with embodiments of FIGS. 2-5 absorbent articles 4 are individually wrapped/packaged. The packaging 6 for an individual absorbent article 4 may be manufactured from the same material as the outer layer 8 of the absorbent article 4. In other embodiments, the packaging 6 may be formed from a plastic film, a moisture impervious woven or non-woven material or other variations of impervious plant, animal, and chemical fiber based materials. The packaging 6 may also include odor eliminating properties.

Figure 2:
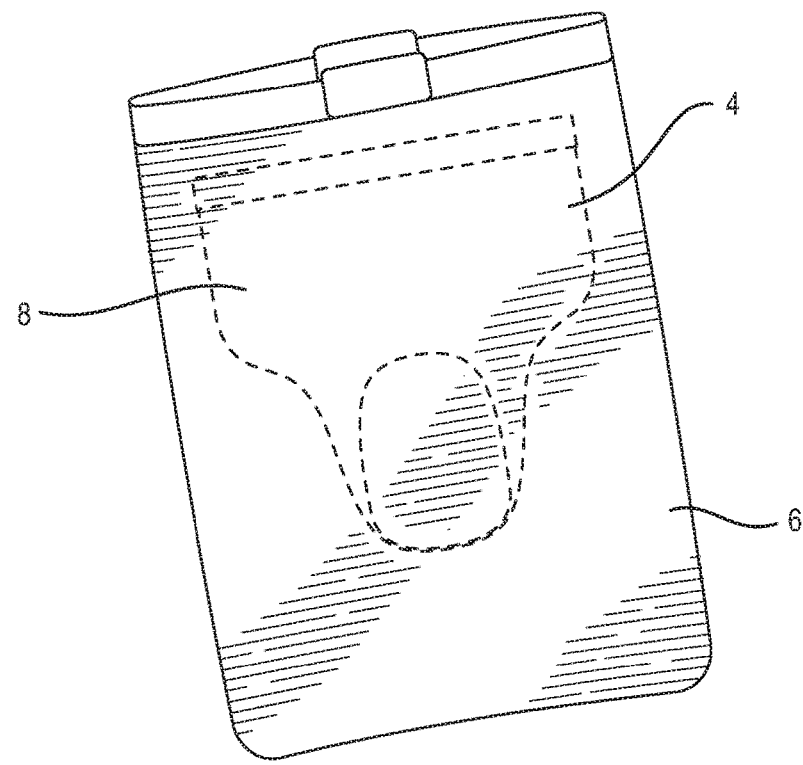
FIG. 2 is a plan view of an unused individual absorbent article contained within an individual packaging unit.

FIG. 3 is a plan view of the individual packaging 6 of FIG. 2 in a sealed, empty condition. FIG. 4 illustrates a cut away view at line A-A of the empty sealed individual package 6. It should be particularly understood that in its initially manufactured condition, the bottom end 10 of bag 6 may be open, and that it is contemplated that bag 6 will be filled by passing the absorbent article 4 through the bottom end 10, rather than through the top end 12 as is the conventional mode of filling a drawstring-type bag. At the bottom end 10 of bag 6, the end edges of the front and back face panels 14, 16 may lie adjacent each other, as illustrated, or one of the face panels may be made slightly longer than the other to provide an extended lip at the bottom end 10 of the bag 6 for facilitating the forming of the bottom end 12 closure, as will be understood by those skilled in the art.

Referring now to the construction at the top end portion 12 of the bag 6, in a first process, a gusset 18 is formed by lines of fold 20, 21 and 22 of the single sheet of material which forms the front and back face panels 14 and 16, thus providing the relatively short interior panels 23 and 24. Interior panel 23 is bounded by the lines of fold 20 and 21 and lies adjacent the front face panel 14 and interior panel 24 is bounded by the lines of fold 21 and 22 and lies adjacent the back face panel 16. Thus, gusset 21 may be considered as being substantially V-shaped towards the interior of the bag 6 at its top end 12, the alternate lines of fold 20 and 23 lying adjacent to each other and providing the extreme top end edge of the bag, these lines extending fully across the width of the bag between its side edges 26 and 28.

Fold 21 extends across the bag width in spaced parallel relation with respect to the lines of fold 20 and 22, and lies between the front and back face panels 14 and 16, but is not attached thereto along its length.

In a further step in the process, respective opposite ends of each of the interior panels 23 and 24 are attached to the respective side edges 26 and 28 of the bag by adhering, bonding, embossing, stitching or other suitable techniques. In the illustrated embodiment, these opposite ends of the interior panels are firmly attached between the face panels 14 and 16 by extensions of the upper ends of the respective side edge seals 30 and 32. It will later be more fully understood that this attachment of the gusset at each of its opposite ends very effectively seals off the interior of the bag 6 at its top end, considering the relationship thereto of the additional lines of seal 34 and 36 which form the respective tubular hems 38 and 40 for receiving the drawstring 42, as will now be described. Seals 30, 32, 34, 36 can be accomplished by adhering, bonding, embossing, stitching and other suitable techniques.

One or more lines of seals 34, 36 extend across the bag 6 width. Seals 34, 36 may be continuous, intermittent or staggered. Seal 34 being disposed in space relation with respect to the interior panel 23 and attaching the latter to the front face panel 14, and seal 36 being disposed similarly with respect to the interior panel 24 and attaching the latter to the back face panel 16, all as will be more fully understood by reference to FIG. 4. As shown more clearly by FIG. 3, seals 34 and 36 are in parallel spaced relation with respect to the respective lines of fold 20 and 22 and with respect to the line of fold 21 so as to provide a pocket along the top end edge of each face panel 14, 16. In the illustrated embodiment, seal 34, 36 extends between the terminal ends 30a, 32b of the side edge seals 30 and 32. It should be understood, however, that the distance between the folds 20 and 22 and respective seals 34 and 36, as measured in the direction of the bag height, need only be such as will form the complementary tubular hems 38 and 40 with equal diameters as will be convenient for slidable passage therethrough of drawstring 42, and that respective lower portions 23a, 24a interior panels 23, 24 may have any convenient height, as by spacing fold 21 at a greater or lesser distance away from seal 34, 36.

Since the respective terminal ends 30a, 32a of side edge seals 30 and 32 are spaced away from folds 20 and 22, to substantially the same extent as are the conjoining lines of seals 34, 36, it will be understood that each of tubular hem 38 and 40 is open at both of its ends. The adjacent open ends of both tubular hem 38 and 40 are respectively indicated by reference numerals 44 and 46.

In a bag filling operation, the bag is opened at its bottom end 10, 11 by drawing apart the adjacent ends of the front and back face panels 14 and 16. An individual absorbent article 4 is inserted into the bag 6. When filled, the bottom ends 10, 11 of the face panels 14 and 16 are drawn together, and sealed 38 together by adhering, bonding, embossing, stitching and other suitable techniques. Thus, the absorbent article 4 is totally enclosed and completely sealed within the bag 6, since neither air, nor liquid, nor moisture can penetrate the seals at the ends of the gusset 18, as previously explained. The bag 6 is then inverted to its right-side-up position and may be freely supported or carried by its drawstring 42, whereupon the weight of the contained absorbent article 6 will cause a puckering of the tubular hems 38 and 40.

In an alternative step to the process, drawstring 42 is applied to an interior surface 52 within fold 22. Interior panel 24 is folded over drawstring segment 42b and heat seal 36 is applied to interior panel 24 and backsheet 16 thus forming tubular hem 40 with fold 21 extending toward bottom end 15. Similarly, a fully formed absorbent article is placed on backsheet 12 in spaced relation between fold 21, side edges 16 and 17 and bottom end 15. Drawstring 29a is applied to an interior surface 11b within fold 20 and the remainder of sheet 11 is folded over drawstring 29a and heat seal 25 is applied to interior panel 23 and front sheet 11 thus forming pocket 27. Side edges 16, 17 and bottom end 15 are sealed as described above.

Placement of the absorbent article on sheet interior surfaces 54 or 56 of front or rear panels 14, 16 may be performed in-line after the absorbent article 4 has been produced. In the alternative, placement of the absorbent article 4 within bag 6 may be by hand after the absorbent article 4 has been produced.

Referring again to FIG. 3, it is seen that perforations 58 may be disposed along the line of fold 21 to facilitate such opening of the sealed bag. Moreover, it will be noted that rupturing of the perforations 58 of fold 21 when opening the sealed bag does not disturb the construction of either of seals 34, 36 or tubular hems 38, 40, and the drawstring 42 remains serviceable condition for subsequent use in closing the now opened mouth of the bag 6, in manner as is conventional.

In the embodiment shown, complementary drawstring segments 42a and 42b; are disposed within each of the respective tubular hems 38, 40 (see FIG. 4), the drawstring portions having equal lengths which are greater than the width of the bag so that they project outwardly of the side edges 26, 28 to be attached together at these locations by methods known in the art. Thus, the complementary drawstring portions 42a, 42b effectively provide a drawstring loop extending through both of the tubular hems 38, 40.

In one embodiment, to provide a more compact assembly, the absorbent article 4 may be vacuum sealed within the bag 6. In an alternative embodiment, prior to insertion into the bag, the absorbent article 4 may be folded once, twice, thrice or more times in order to reduce volume/bulk. The absorbent article 4 can then be inserted into the bag 6 and sealed as described above. Alternatively, the folded absorbent article 4 may be vacuum sealed within the bag 6.

In accordance with embodiments of the present invention, packaging 6 for an individual absorbent article 4 has an area that is at least one, two, three or more times the area of an absorbent article 4. Accordingly, the excess volume of the packaging 6 is folded over the shape of the absorbent article 4 resulting in a compact packaging/absorbent article assembly which is inserted into retail packaging 2 or removed from retail packaging 2 for transport and later use.

Manufacturing of embodiments of the present invention will include those steps employed in manufacturing an absorbent article as would be understood by one of ordinary skill in the art with the addition of those steps necessary to create packaging for an individual absorbent article and with the addition of those steps necessary to fill packaging with an individual absorbent article.

In use, an individually packaged absorbent article assembly is removed from the retail packaging 2 including a plurality of individually packaged absorbent articles. The individual package 6 perforated seal 58 is ruptured and absorbent article 4 is removed and then donned by the user. The assembly packaging 6 (now empty) may be folded and stowed (in a pocket for later use). Optionally, the assembly packaging 6 may be discarded and another individually wrapped absorbent article 4 may be selected for later use.

The user may now engage in the activities of daily life. Once the absorbent article 4 becomes soiled by body discharges, the user removes the soiled article 60, opens the packaging 6 which originally contained an unused absorbent article 4, and inserts the soiled absorbent article 60 into the packaging. The drawstrings 42 of the packaging 6 are gathered as illustrated in FIG. 5. The user then ruptures the seal 58 on another individually packaged absorbent article assembly, and an absorbent article is removed and then donned by the user. The packaging 62 containing the soiled absorbent article 60 is now ready for disposal.

Aesthetically, the packaging 6 resembles other articles a user might carry, for example shopping bags. Accordingly, the packaging 6 is not limited to any particular color, size or style. In accordance with embodiments of the invention the packaging 6 may be designed to not look like it contains an absorbent article 4. In fact, the packaging 6 volume may exceed the volume of a body discharge soiled absorbent article 60 by one, two, three or more times.

The packaging 6 for an individually wrapped absorbent article 4 may be constructed from among a plurality of materials as is known in the art, including but not limited to plastic films, cloth and cloth like fibers, woven and nonwoven materials, et al.

To aid in noise reduction, the packaging 6 may be manufactured from the same material as the outer layer of the absorbent article 4. The packaging 6 may have a soft touch and thus produce minimal noise when handled, such as when opening or closing.

In an embodiment, the assembly packaging 6 may include indicia 64. In one alternative, indicia 64 may announce the packaging 6 contents. In a further alternative, indicia 64 may mislead viewers as to the contents of the assembly packaging. For example, indicia 64 could include phrases, "Thank you" or "Come again soon" or other phrases that a retailer might include on a shopping bag. Other examples could include pictorial indicia such as smiley faces or the "reduce, reuse, recycle" icon. Other examples could include co-marketed advertising. Other examples could include any other indicia 64 to distract from the actual packaging 6 contents.

In accordance with embodiments of the present invention, the packaging 6 for an individually wrapped absorbent article 4 may include deodorizers, perfumes and the like to help mask odors which may permeate from body discharges contained within a soiled absorbent article 60.

Figure 6:
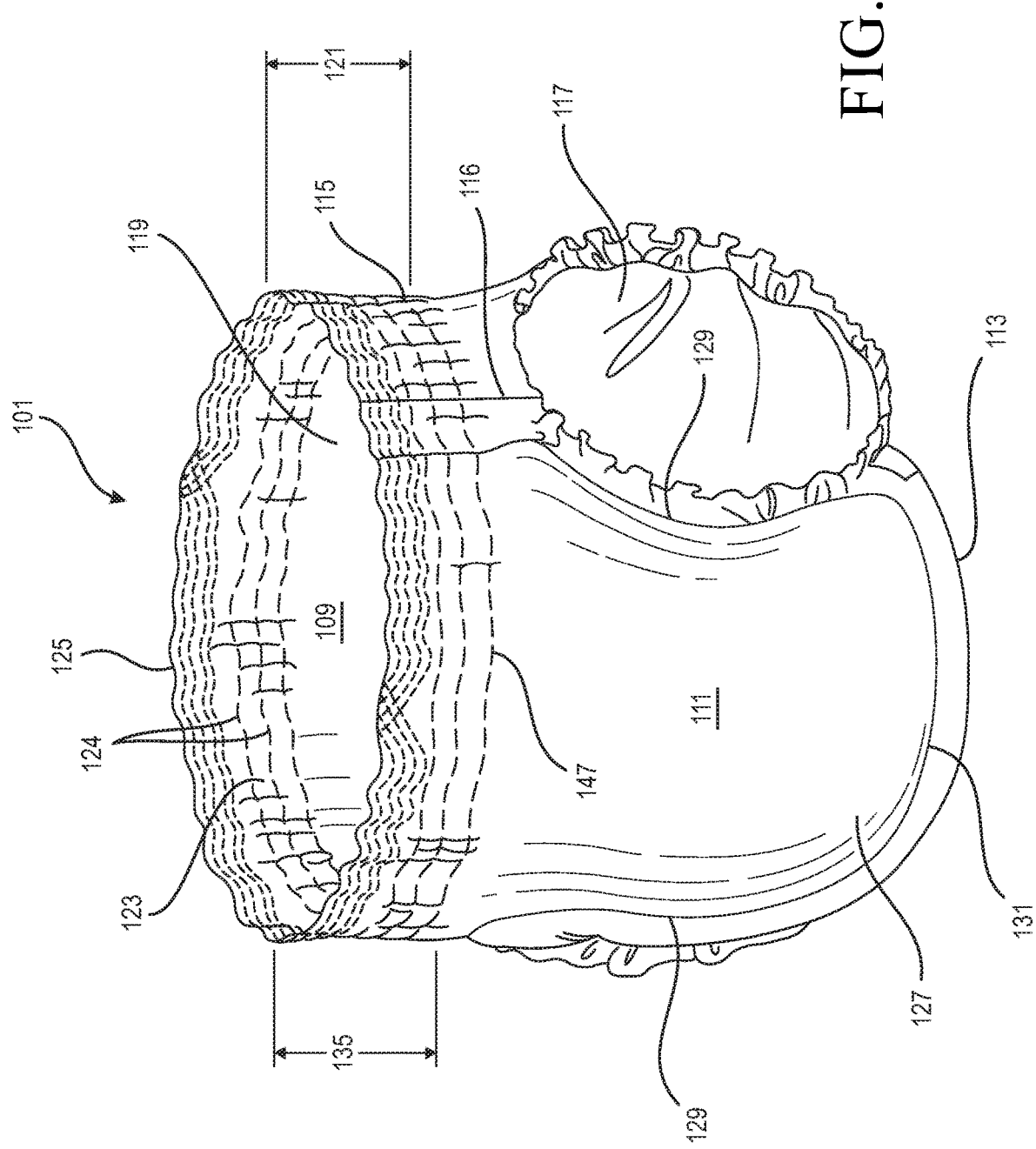
FIG. 6 is a rear perspective view of a disposable absorbent article in a use condition.
Figure 7:
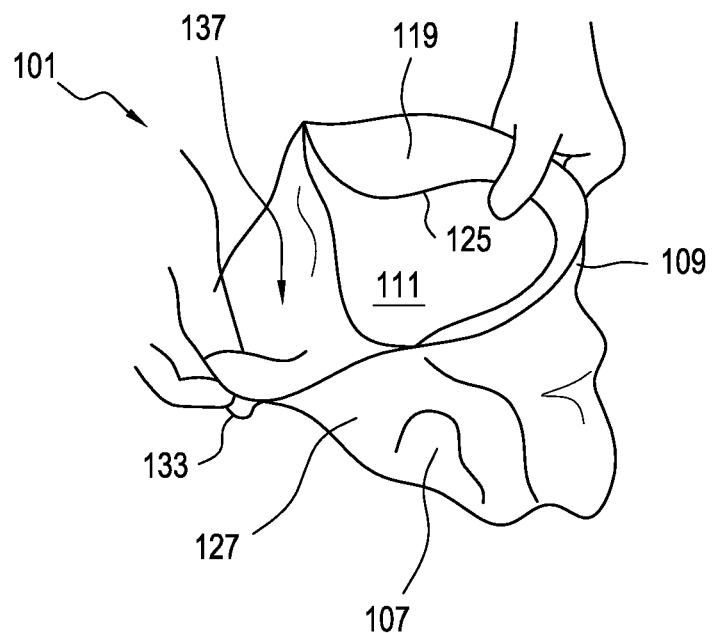
FIG. 7 is a top perspective view of the absorbent article of FIG. 6 illustrating the pouch opening extended away from the rear portion of the absorbent article.

FIG. 6 illustrates a disposable absorbent article 101, more particularly, a disposable brief. The absorbent article 101 generally includes several layers: a moisture-impervious outer layer 107, an inner layer 103 substantially co-extensive with the outer layer and one or more absorbent layers 105 interposed between the inner layer 103 and outer layer 107.

The inner layer 103 may be composed of a moisture-pervious fabric suitable to allow body discharges to pass through the inner layer 103 and be absorbed by the absorbent layer 105. Non-limiting examples of materials suitable to form the inner layer 103 include polypropylene, polyethylene, polyester, materials having hydrophobic properties, combinations thereof and/or the like. Additionally, the inner layer 103 can be treated with a hydrophilic finish to improve passage of fluids through to diaper layers beneath the inner layer 103. Non-limiting examples of suitable hydrophilic finishes include stearic acid, melamine-based chemicals, fluorocarbon chemicals, and silicon based chemicals.

The outer layer 107, which faces away from the wearer, is composed of a moisture-impervious fabric. Accordingly, the outer layer 107 may be made of any material suitable to minimize or prevent biomatter from escaping the absorbent article 101. Non-limiting examples of suitable materials for the outer layer 107 include polyethylene or other polymer materials and may be breathable.

Figure 10:
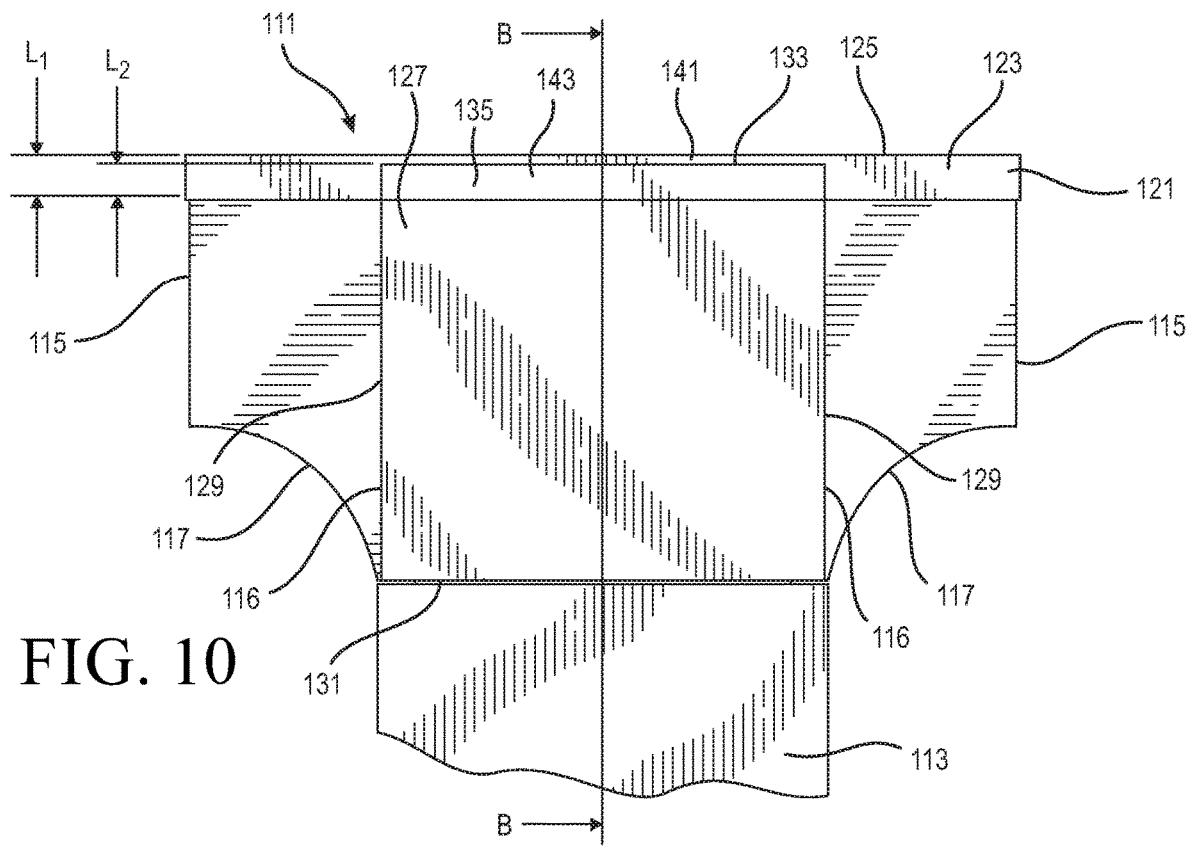
FIG. 10 is a plan view of the rear portion of the absorbent article and pouch of FIG. 6.
Figure 13:
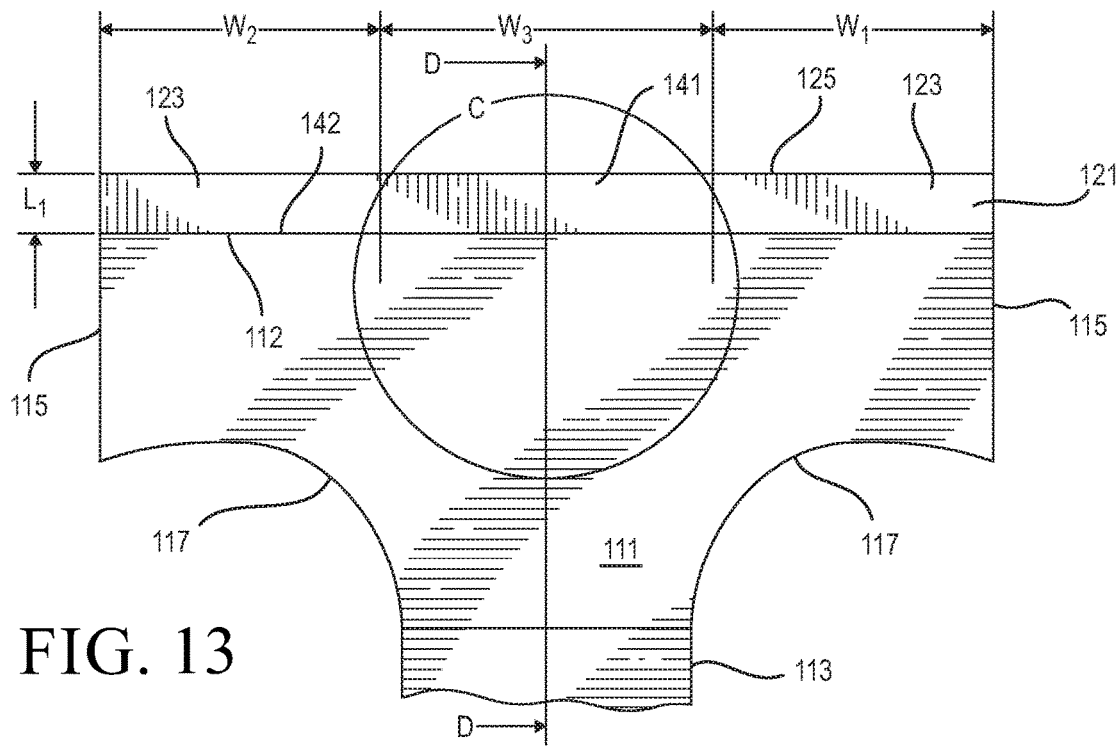
FIG. 13 is a plan view of an embodiment of a rear portion of the absorbent article of FIG. 6 illustrating waist margin structure in a closed/undeployed condition.

The absorbent article 101 may include a chassis having a first portion 109, a second portion 111 and a center portion 113 connected there between. The first and second portions may include a plurality of side panels 115 corresponding with a wearer's hip region, the side panels 115, which when joined to the first portion 109 and second portion 111 form first and second leg openings 117 and a waist opening 119. In embodiments of the absorbent article, as illustrated in FIG. 10, the side panels may be separate elements 115 attached to the chassis first portion and second portion 111 along side edges 116 of the first and second portion. Alternatively, as illustrated in FIG. 13, side panels 115 may be integrally formed with the first and second chassis portions. In an embodiment, the leg openings may be integrally elastic or may include applied elastics.

In one embodiment, the plurality of side panels includes two side panels with a first side panel first end connecting a left side of the first portion and a first side panel second end connecting a left side of the second portion, and a second side panel first end connecting a right side of the first portion and a second side panel second end connecting a left side of the second portion. In a further embodiment, the plurality of side panels may include four side panels. In such an example, the side panels may further include side seams or a fastener system known in the art for joining first and third side panels together with respective left side portions of the first and second side portions and joining second and fourth side panels with respective right side portions of the first and second side portions.

While a brief style absorbent article 103 is depicted, those skilled in the art will recognize that bikini, boxer, boxer brief and other styles of absorbent articles (for example, disposable pads, napkins, diapers, training pants) can be implemented without departing from the scope of the embodiments disclosed herein.

The first portion 109 and the second portion 111 may encompass a single layer of material, or may be a laminate material.

In an embodiment, the absorbent article 101 may include aesthetically pleasing color features so as to suggest that the article resembles the color features of traditional undergarments. By way of non-limiting example, the article may be buff colored, gray, or include a multi-colored pattern, designs or indicia.

As illustrated in FIGS. 6, and 8-10, the waist opening 119 includes a circumferential waist margin 121 forming a waist band 123. In some embodiments, the waist band 123 is elastomeric. Elasticity may be imparted by applying elastic ribbons, tapes and the like to the waist band 123, or elasticity may be integral to the absorbent article 101 generally. In some embodiments, the waist band is integral to the first portion 109, second portion 111 and side panels 115.

Figure 27:
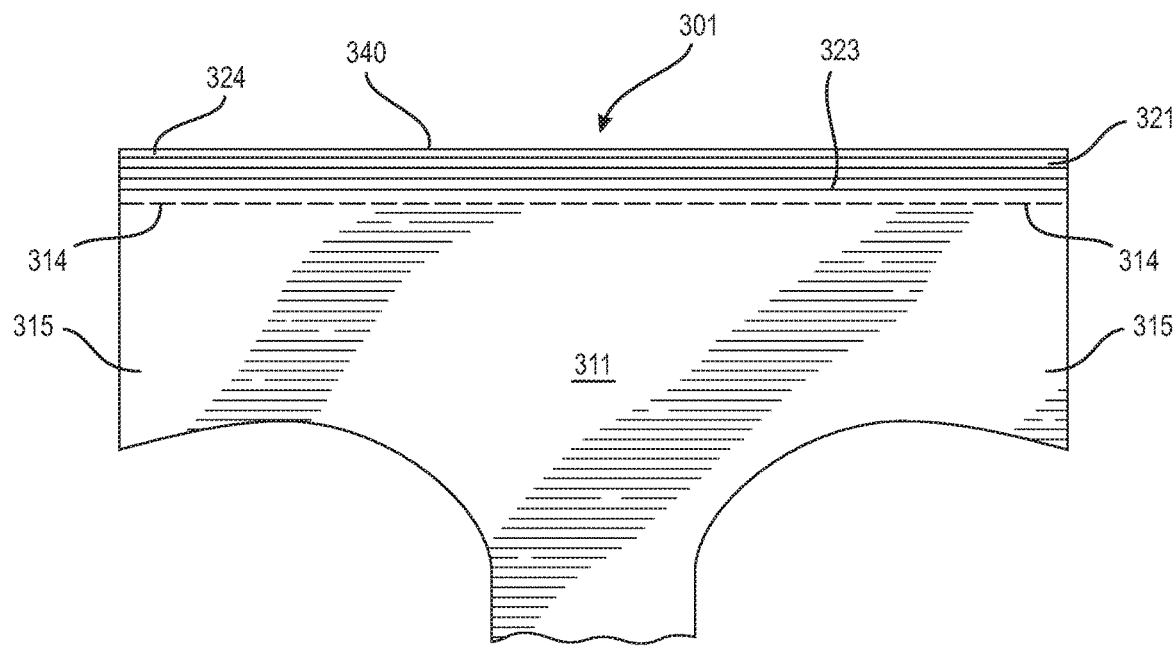
FIG. 27 is a plan view of an embodiment of a rear portion of an absorbent article in which the waist band circumferential margin is cantilevered from the rear portion.

In some embodiments, as illustrated in FIG. 27, the absorbent article 301 may include a waistband 323, including a circumferential margin 321 that is attached to first portion top edge (not shown), second portion 311 top edge 312 and side panel 315 top edges 314. A top edge 340 of the waistband 323 extends longitudinally from the top edges of the first portion top edge, second portion top edges 312 and side panels top edges 314 such that the waist band 323 and circumferential margin 321 are cantilevered off of the first portion second portion 311 and side panels 315.

Figure 28:
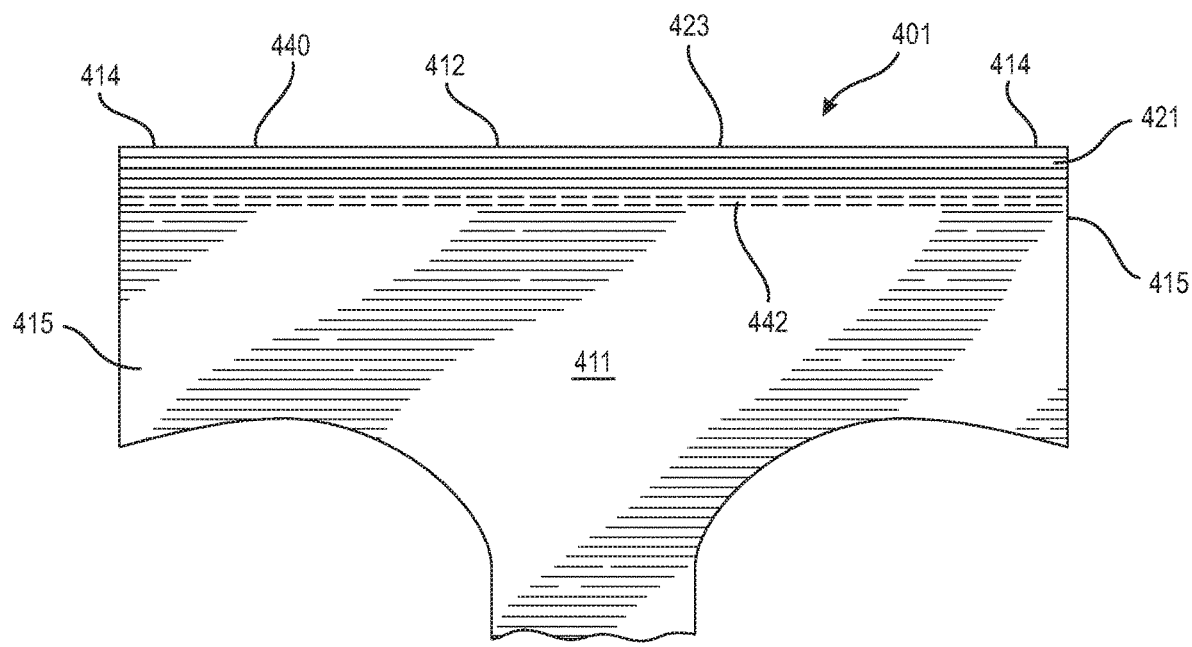
FIG. 28 is a plan view of an embodiment of a rear portion of the absorbent article of FIG. 6 in which the waist band circumferential margin is coterminous with a top portion of a rear portion of an absorbent article.

In some embodiments, as illustrated in FIG. 28, the absorbent article 401 may include a waistband 423, including a circumferential margin 421 is attached to first portion (not shown), second portion 411 and side panels 415 such that a top edge 440 of waist band 423 and top edges 412 of the front and rear portions 410 and 411 and side panel top edges 414 are coterminous.

Figure 8:
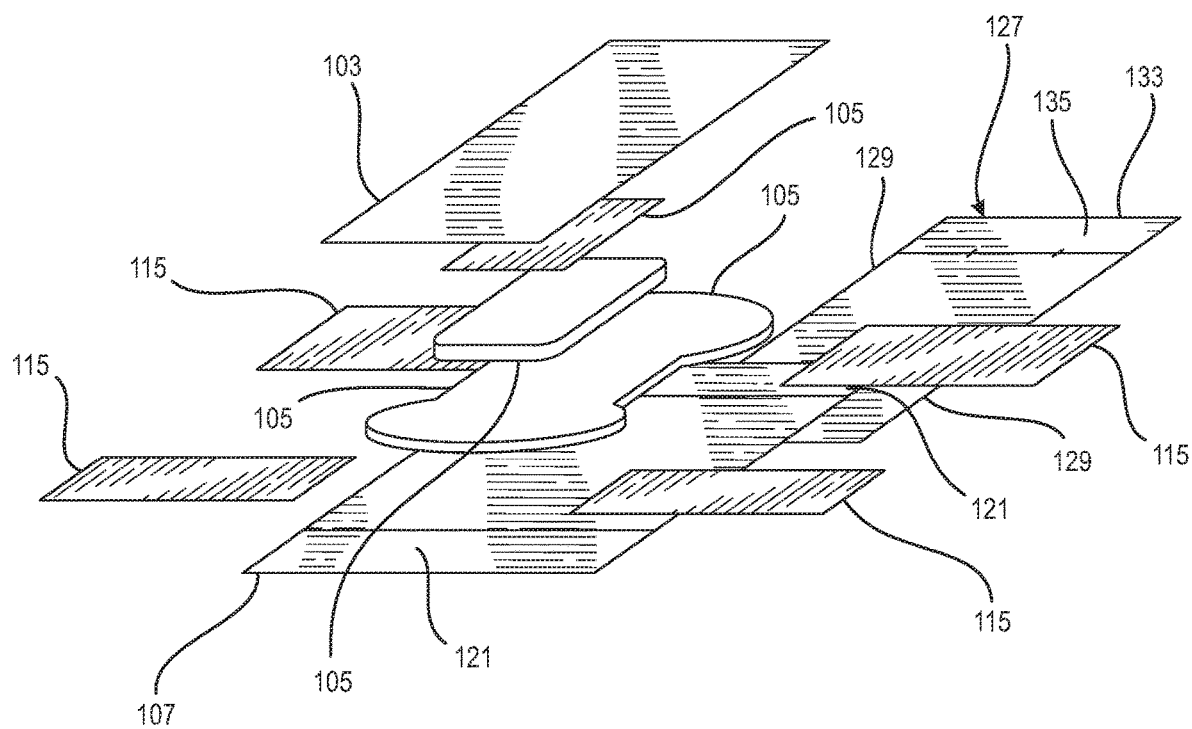
FIG. 8 is an exploded view of the absorbent article of FIG. 6 in an open, flat condition.
Figure 9:
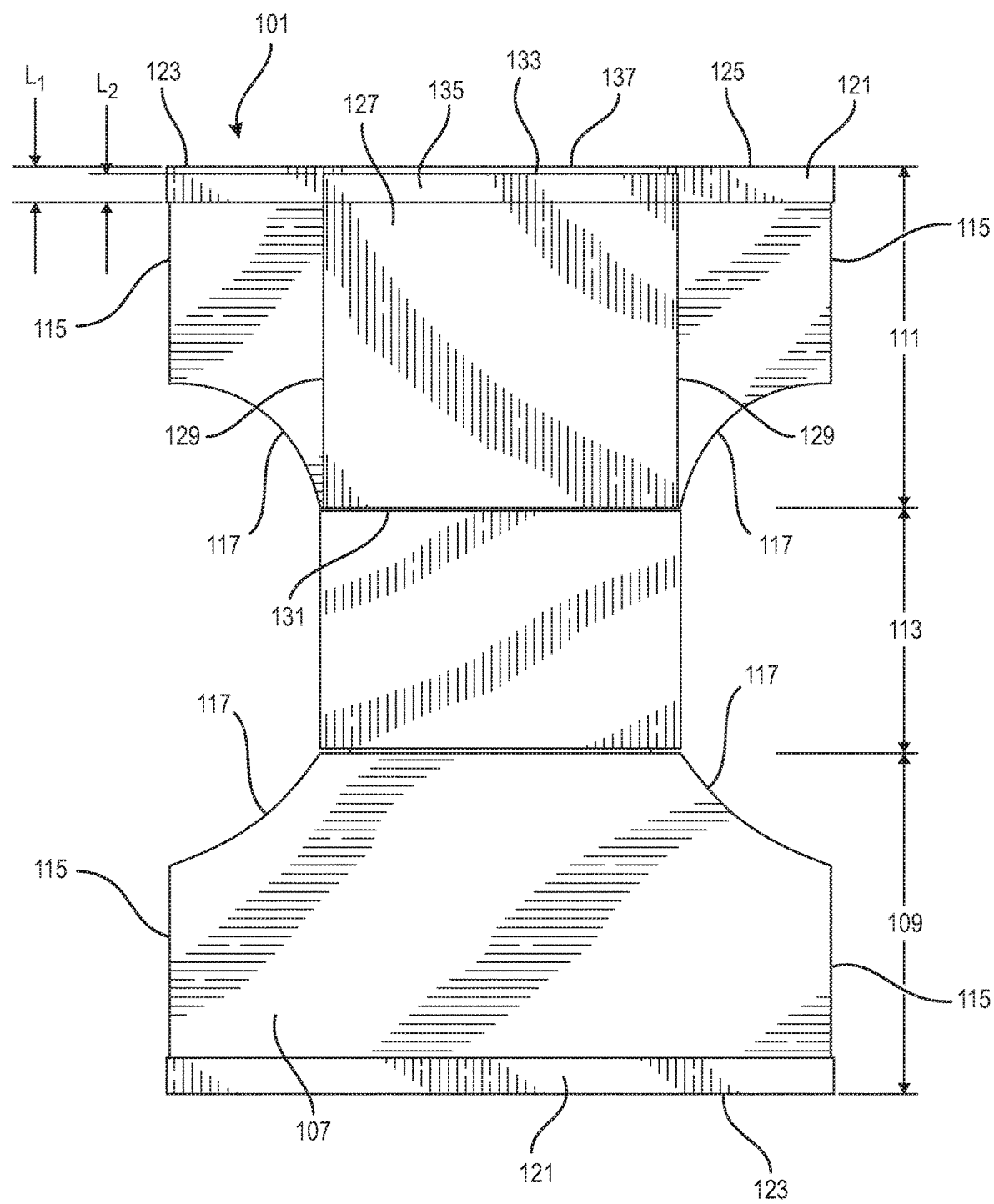
FIG. 9 is a plan view of the absorbent article of FIG. 6.

FIG. 8 is an exploded view of the absorbent article 101 in an open, flat condition, with certain items removed for clarity. Adjacent to the second portion 111 of the absorbent article 101 a pocket or pouch 127 is attached to or is integral to the outside surface of the absorbent article 101. In an alternative embodiment (not illustrated), the pouch may be attached to or integral to the first portion 109. The pouch 127 may be constructed from the same material as the outer layer 107, or may be constructed from any suitable material as is known in the art. In some embodiments, the absorbent article 101 may include odor masking or eliminating properties. In some embodiments, the pouch 127 is extensible along any of an x, y and z axis. Preferably, the pouch 127 will extend one, two, three or more times beyond a flat, normal condition along at least one of an x, y, and z axis.

As illustrated in FIG. 10, pouch 127 includes side walls 129 running parallel in spaced relation to the first and second side panels 115, transverse to the waist opening 119; a bottom wall 131 which terminates along a lower portion of the second portion 111 in spaced relation between the center portion 113 and the waist opening 119; and a top portion 133 forming an opening 137 between the pouch 127 and the absorbent article 103 rear portion 111 outer layer 107. The sidewalls 129 may parallel the side edges 116 of the chassis second portion 111. In one embodiment, the pouch opening 137 is aligned with an edge portion 125 of the waist opening 119. Alternatively, the pouch opening 137 may be in spaced relation between the waist opening 119 and the pouch bottom wall 131. Said differently, the pouch opening 137 may be below the waist opening 119.

Figure 29:
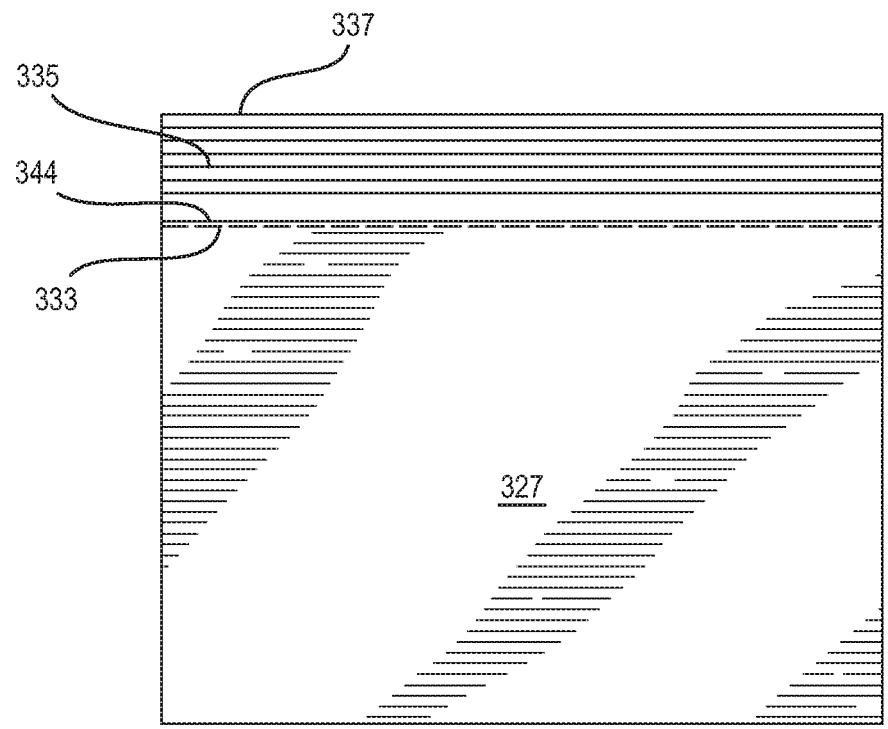
FIG. 29 is a plan view of an embodiment of a pouch portion of an absorbent article in which the pouch margin is cantilevered from a pouch of an absorbent article.
Figure 30:
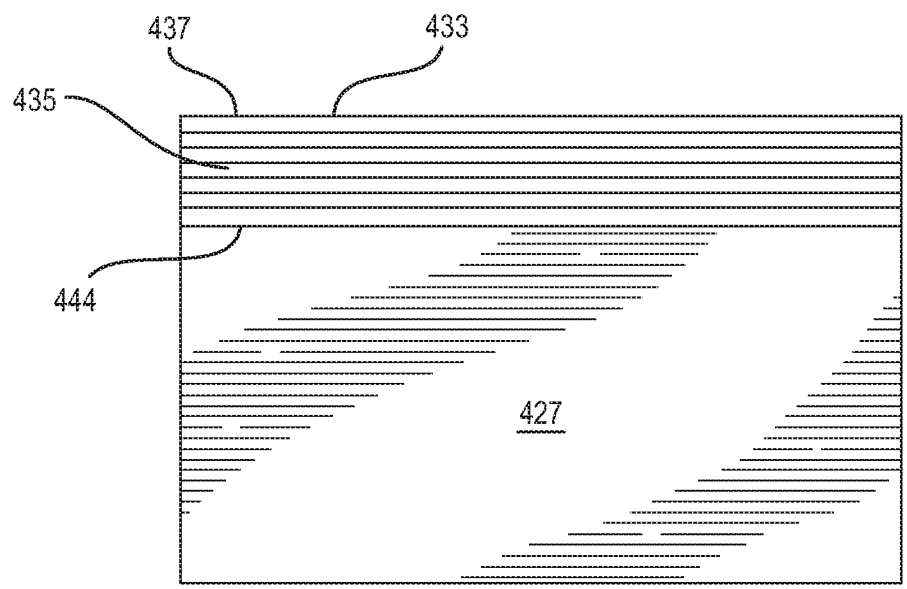
FIG. 30 is a plan view of an embodiment of a pouch portion of an absorbent article in which the pouch margin is coterminous with a top portion of a pouch of an absorbent article.

In some embodiments, the pouch margin 135 and the waist margin 121 may be similarly constructed. FIG. 29 illustrates a cantilevered pouch margin constructed using the same techniques as the cantilevered waist margin of FIG. 27 and FIG. 30 illustrates a pouch including a coterminous margin constructed using the same techniques as the coterminous waist margin of FIG. 28. In alternative embodiments, the pouch margin 135 may be constructed from a single material whereas the waist margin 135 may be a laminate material.

As illustrated in FIG. 13, second portion 111 waist margin 121 longitudinal extension is defined by segment $L_1$ and lateral extension is defined by segments $W_1$, $W_2$, and $W_3$, in which segments $W_1$ and $W_2$ define the outermost segments, with segment $W_3$ lying between segments $W_1$ and $W_2$. In an embodiment, distance spanned by segments $W_1$ and $W_2$ is substantially equal, and the distance spanned segment $W_3$ is less than the distance spanned by segments $W_1$ and $W_2$. In an alternative embodiment, the distance spanned by segments $W_1$, $W_2$ and $W_3$ is substantially equal. In a further alternative, the distance spanned by segments $W_1$ and $W_2$ is less than the distance spanned by segment $W_3$. In a still further alternative, none of the distances spanned by segments $W_1$, $W_2$ or $W_3$ is equal.

As illustrated in FIG. 10, pouch top portion 133 includes a margin 135. Pouch margin 135 and waist margin 121 are similarly constructed. In an embodiment the waist margin and the pouch margin are respectively integral to the rear portion and the pouch. In an alternative embodiment, the waist margin and the pouch margin are respectively attached to, applied to or mounted on the rear portion and the pouch. Application methods may include adhesive, bonding, welding, embossing, stitching, and other techniques suitable in the art.

In some embodiments, the pouch side wall 129 and bottom wall 131 are attached to the outer layer 107 by one or a combination of an adhesive, bonding, welding, embossing, or stitching techniques, or otherwise applied or mounted to the absorbent article outer layer 107. The techniques for attaching the pouch 127 to the outer layer 107 may be applied in a uniform, random or intermittent pattern. In alternative embodiments, the pouch 127 is integrally formed with the absorbent article 101.

Figure 11:
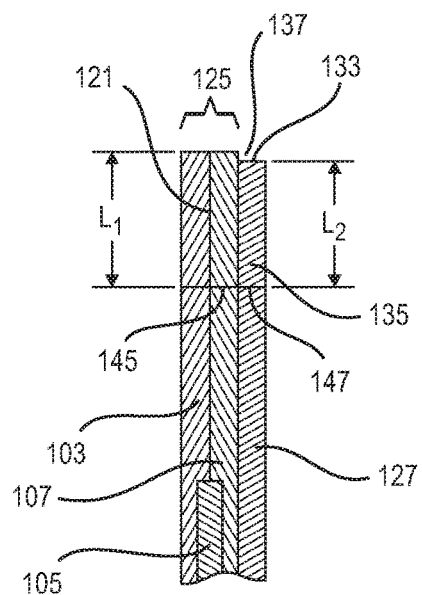
FIG. 11 is a cross-sectional view of an embodiment of the rear portion of the absorbent article FIG. 10 at B-B in an unused condition.
Figure 12:
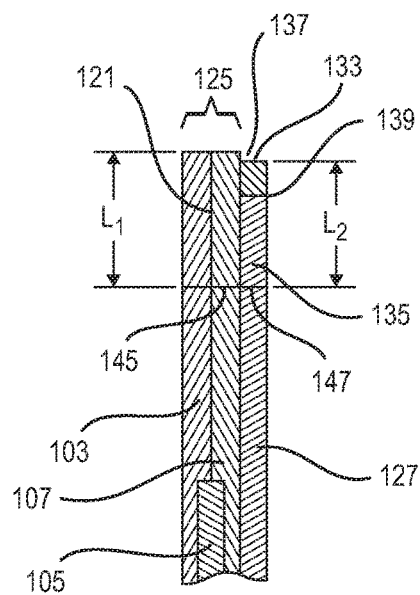
FIG. 12 is a cross-sectional view of the embodiment of FIG. 10 at B-B in an unused condition and including a sealing element.

In the embodiment of FIG. 11, the pouch opening 137 is not sealed against the outer layer 107. In accordance with the embodiment of FIG. 12, the pouch opening 137 is sealed 139 against the outer layer 107 so that the pouch 127 remains in a flat, closed condition until ready for use. By sealing 139 the pouch opening 137, the absorbent article 101 maintains a smooth, discreet profile. The pouch opening 137 may be releasably adhered, bonded or otherwise releasably affixed against the outer layer 107 so as to not damage the pouch 127 or outer layer 107 when the seal 139 is broken. Alternatively, the seal 139 could be mechanical, such as a hook and loop closure, tongue and groove closure, snaps, buttons, hook and eye or other fastening structures. In a further alternative, the pouch opening 137 could be sealed against the outer layer 107 by a releasable tab or ribbon (not shown) which is torn away to reveal the pouch opening 137.

Figure 18:
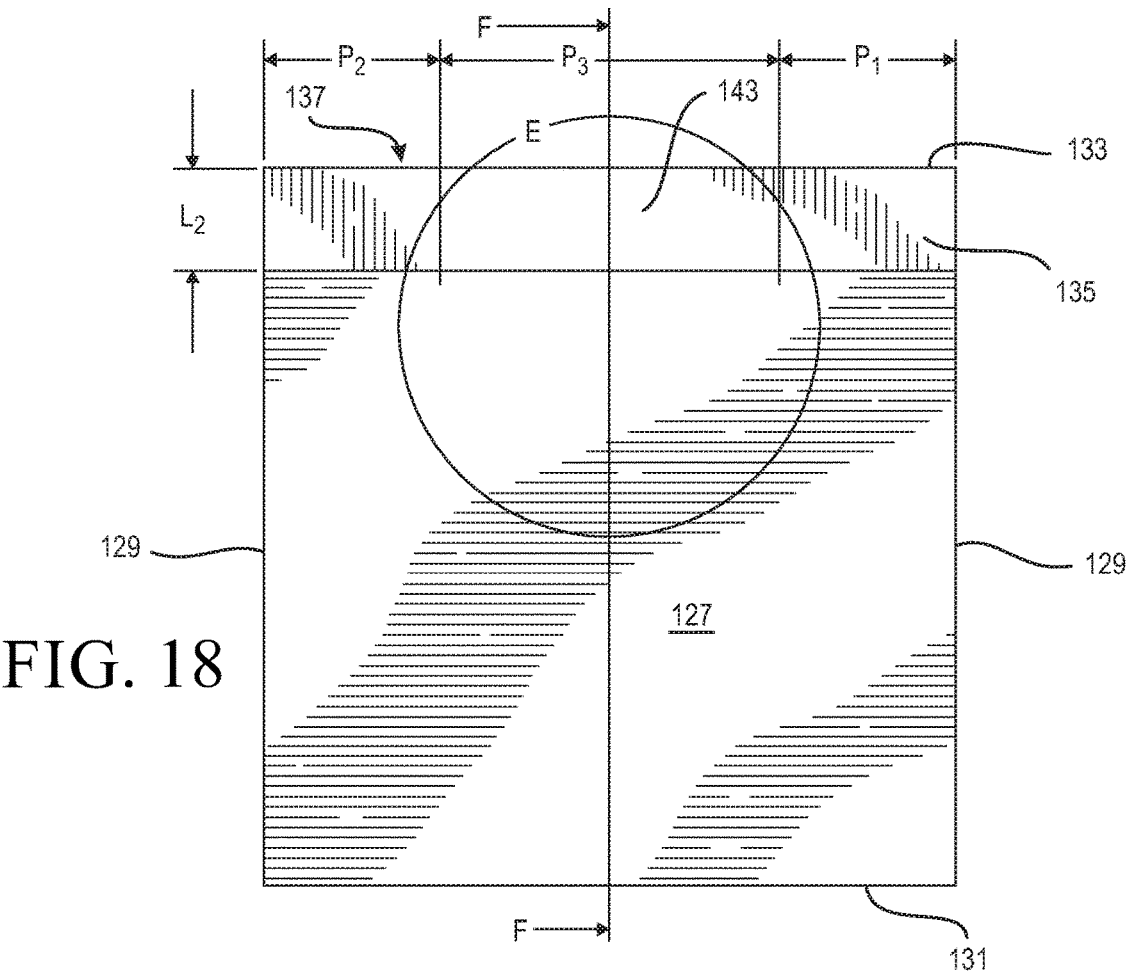
FIG. 18 is a plan view of an embodiment of the pouch portion of the absorbent article of FIG. 6.
Figure 19:
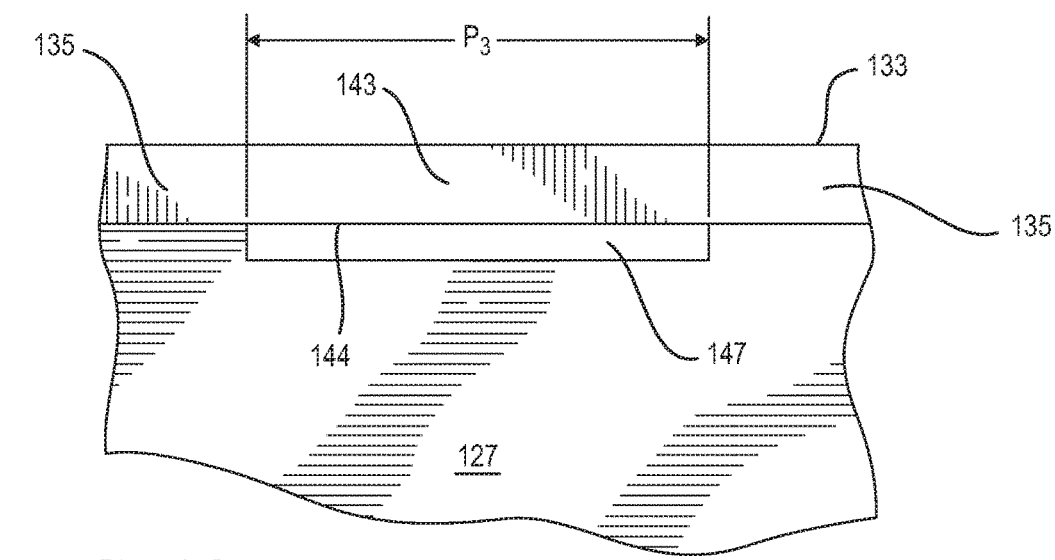
FIG. 19 is an enlarged view of detail E of the embodiment of FIG. 18

As illustrated in FIG. 18, the longitudinal extension of pouch margin 135 is defined by segment $L_2$ and preferably corresponds with (that is substantially equal to) the longitudinal extension $L_1$ of the waist margin 121. In an alternative embodiment, the longitudinal extension $L_2$ of pouch margin 135 and the longitudinal extension $L_1$ waist margin 121 are not corresponding. Pouch margin 135 extends laterally to each of the pouch side walls 129. As illustrated in FIG. 18-19, pouch margin 135 lateral extension is defined by segments $P_1$, $P_2$, and $P_3$, in which segments $P_1$ and $P_2$ define the outermost segments, with segment $P_3$ lying between segments $P_1$ and $P_2$. In an embodiment, distance spanned by segments $P_1$ and $P_2$ is substantially equal, and the distance spanned segment $P_3$ is less than the distance spanned by segments $P_1$ and $P_2$. In an alternative embodiment, the distance spanned by segments $P_1$, $P_2$ and $P_3$ is substantially equal. In a further alternative, the distance spanned by segments $P_1$ and $P_2$ is less than the distance spanned by segment $P_3$. In a still further alternative, none of the distances spanned by segments $P_1$, $P_2$ or $P_3$ is equal. In a preferred embodiment, the distance spanned by $P_3$ may be substantially equal to $W_3$ with the outer limits of P3 and W3 being substantially in linear spaced relation with one another. Said differently, the center points of $P_3$ and $W_3$ are substantially aligned.

Figure 15:
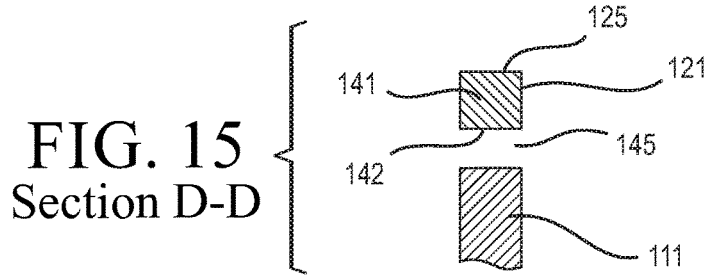
FIG. 15 is a cross-sectional view of the embodiment of FIG. 13 at D-D.
Figure 14:
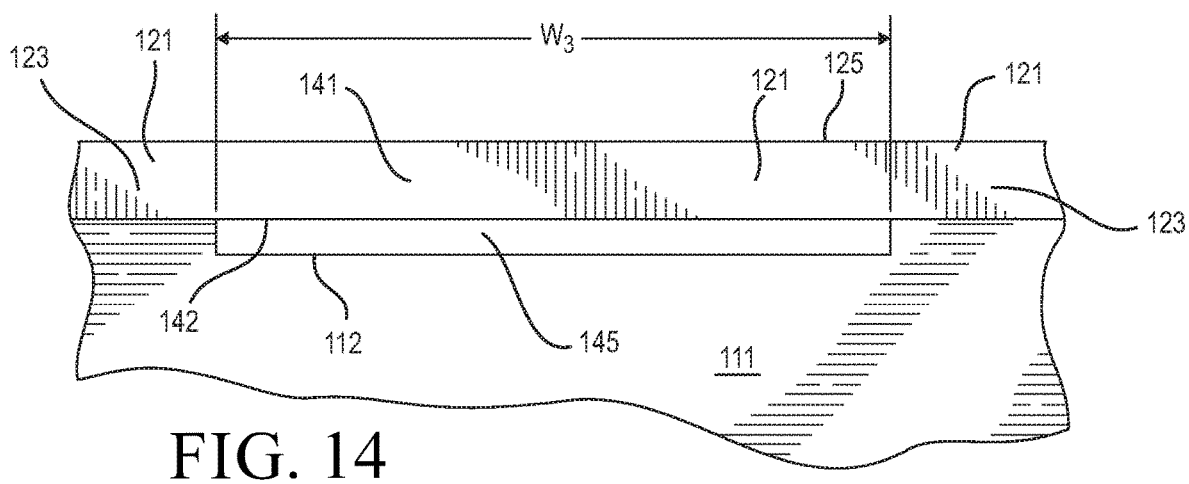
FIG. 14 is an enlarged view of detail C of the embodiment FIG. 13.
Figure 20:
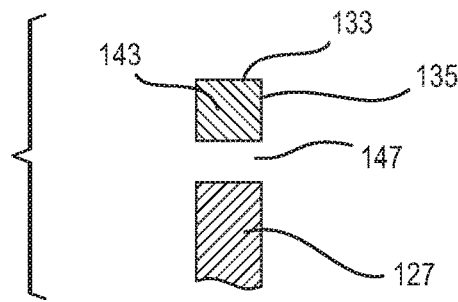
FIG. 20 is a cross-sectional view of the embodiment of FIG. 19 at F-F.

As illustrated in the embodiments of the various figures, the pouch margin 135 and second portion 111 waist margin 121 include handle structures 141, 143. In accordance with the various embodiments, the handle structures are respectively defined by the distances $W_3$ and $P_3$. In the embodiment of FIGS. 13-15, waist margin 121 handle 141 may be formed as a void or slit 145 formed between a lower edge portion 142 of the waist margin 121 and a top edge portion 112 of the second portion 111. Waist margin 121 handle 141 is bound between portions $W_1$ and $W_2$ of waist band 123. As illustrated in FIGS. 18-20, pouch 127 handle 143 may be similarly formed as a void or slit 147 formed along a lower edge portion 144 of pouch margin 135 of pouch 127. As indicated above, owing to the alignment of $P_3$ and $W_3$, pouch void 147 and the waist void 145 are corresponding. In an alternative embodiment (not shown), the voids or slits may be longitudinally positioned in spaced relation within the longitudinal distance L1, L2 spanned by waist margin 121 and pouch margin 135. In a further embodiment, not illustrated, the voids may be "O" shaped, "X" shaped or any other shape suitable for receiving at least one of a human finger, fingers or hand.

Figure 16:
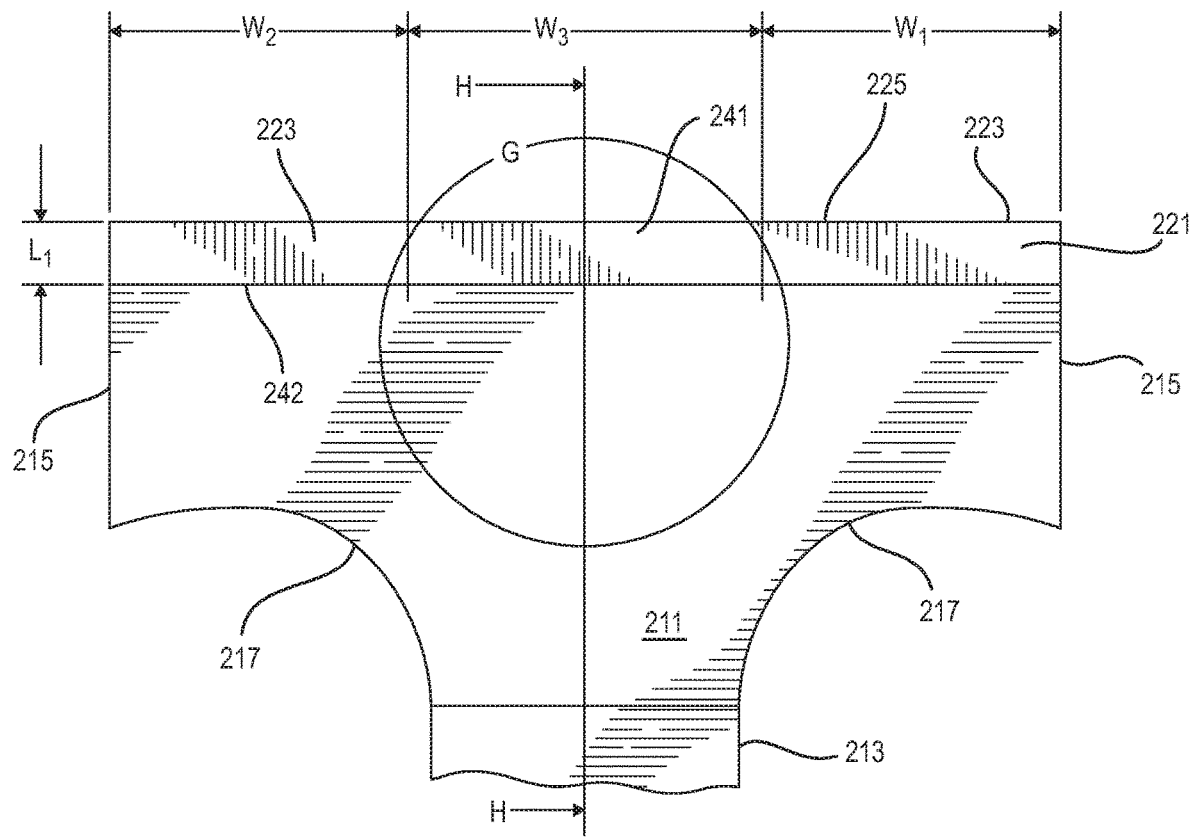
FIG. 16 is a plan view of an alternative embodiment of a rear portion of the absorbent article of FIG. 6 illustrating waist margin structure in a closed/undeployed condition.
Figure 17:
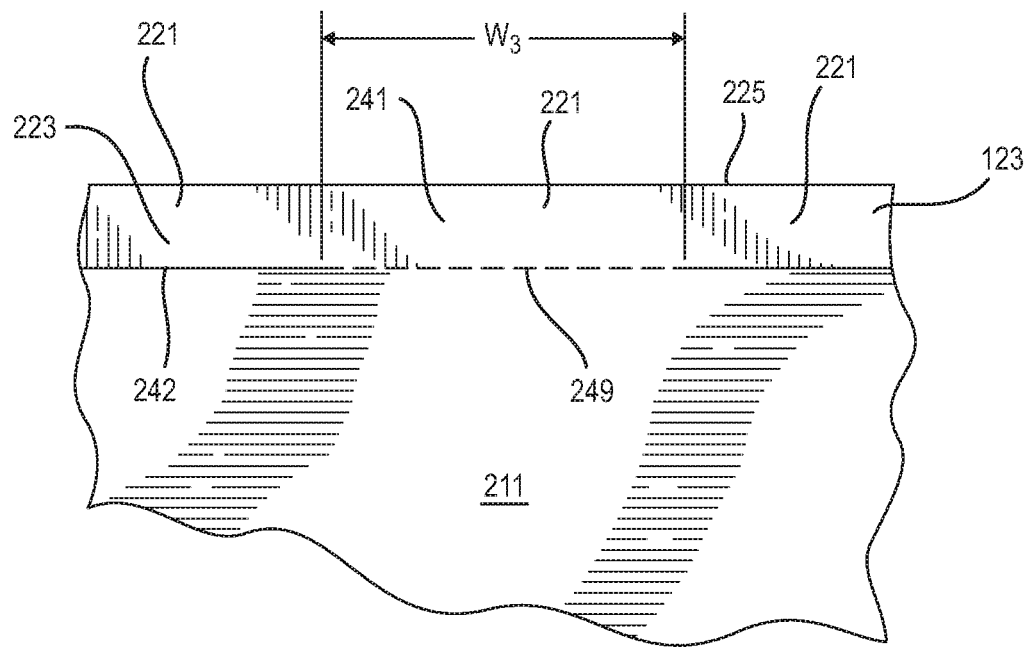
FIGS. 17-17A are enlarged views of detail G of the embodiment FIG. 16.
Figure 17A:
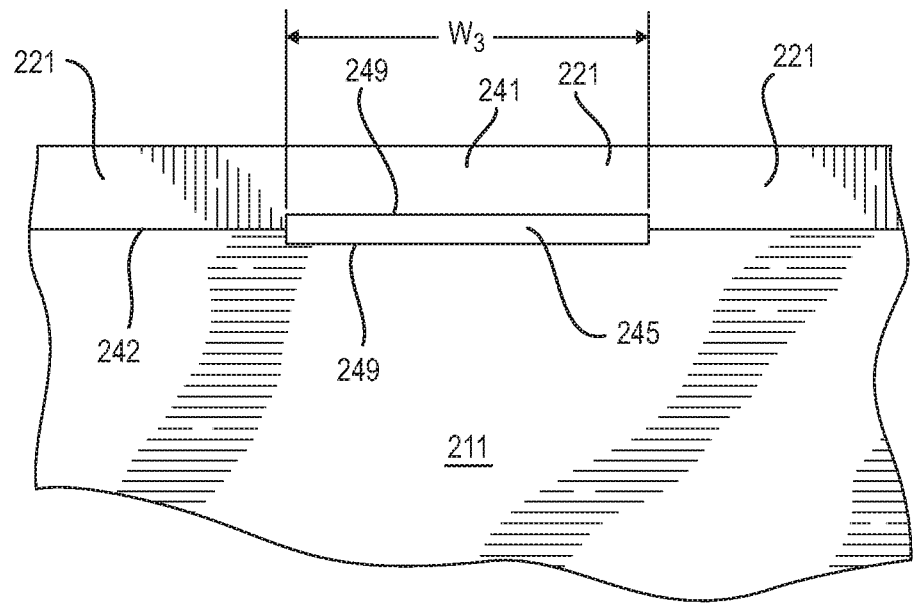
Figure 21:
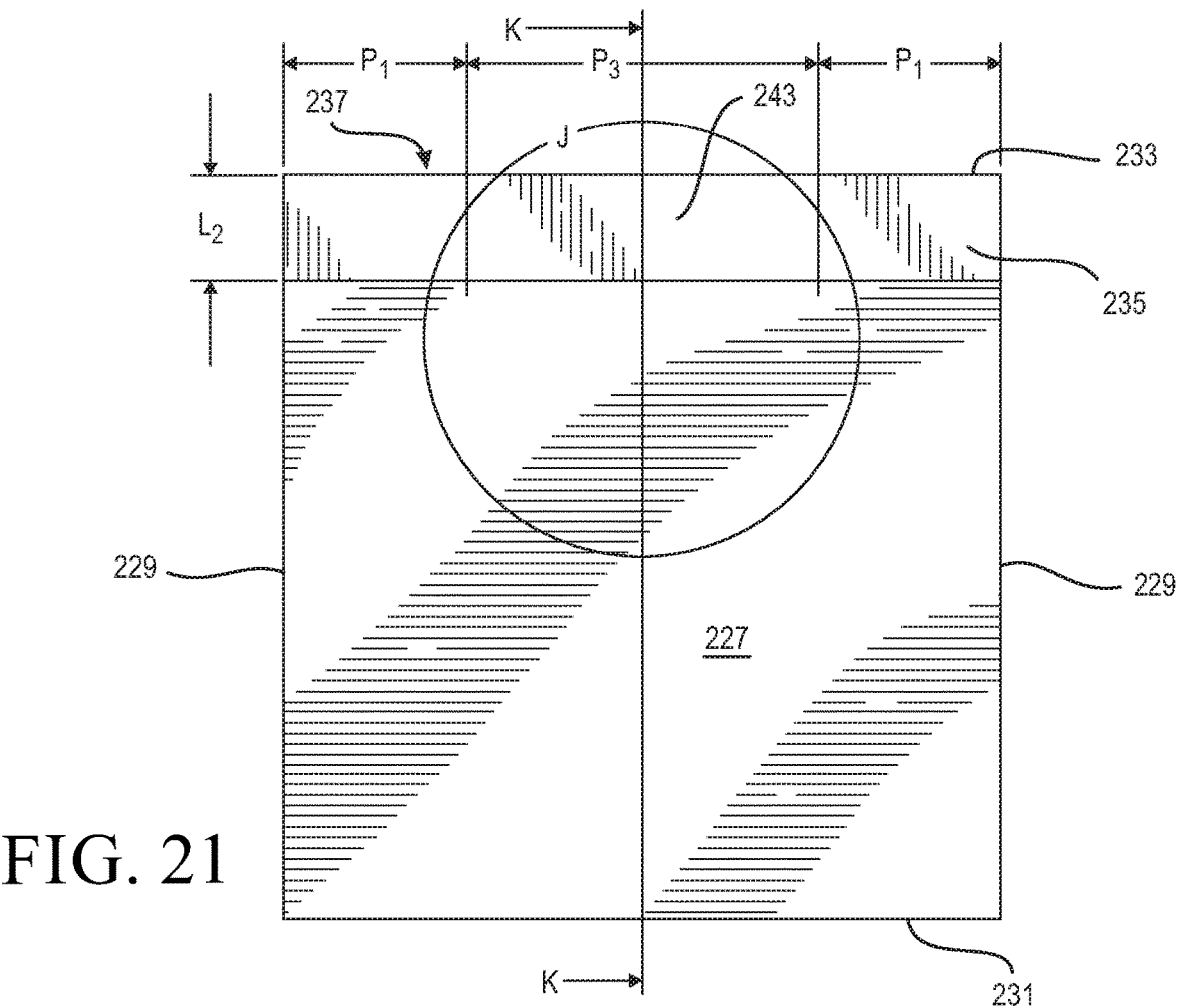
FIG. 21 is a plan view of an alternative embodiment of the pouch portion of the absorbent article of FIG. 6.
Figure 22:
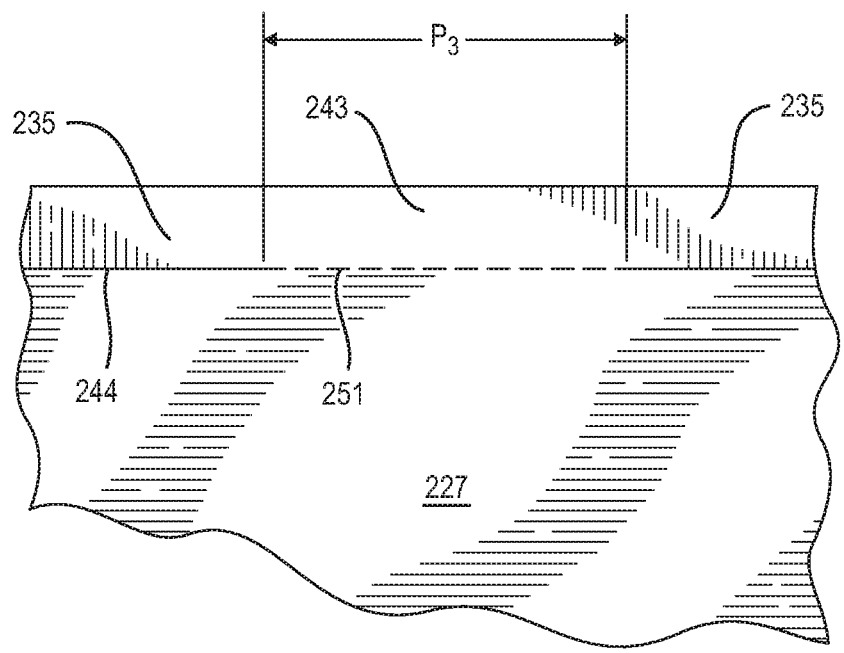
FIGS. 22 and 22A are enlarged views of detail J of the embodiment of FIG. 21.
Figure 22A:
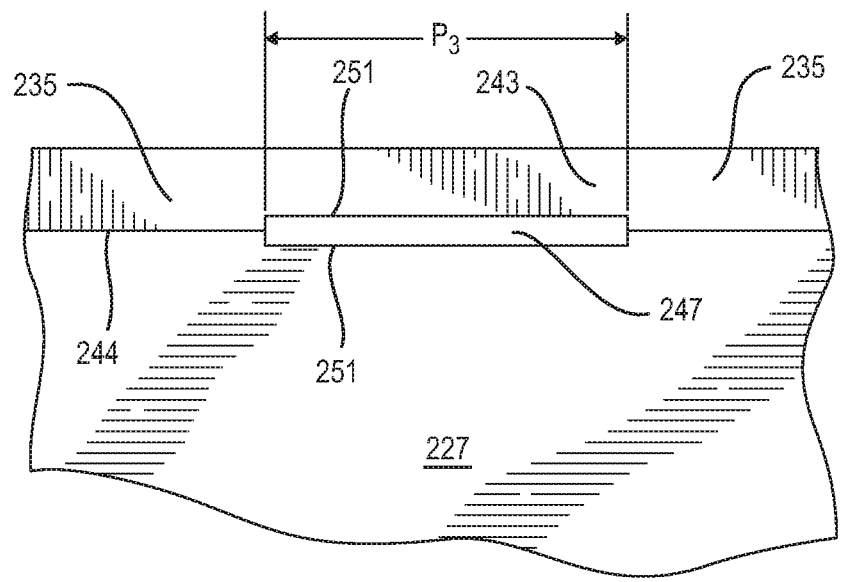

In an alternative embodiment, illustrated among FIGS. 16-17A, waist margin 221 lower edge portion 242 includes a frangible or perforated portion 249 along segment $W_3$. Frangible portion 249, which when ruptured forms void or slit 245 transforming the now detached waist margin 221 segment $W_3$ into handle structure 241. Similarly, as illustrated among FIGS. 21-22A, pouch margin 235 lower edge portion 244 includes a frangible or perforated portion 251 along segment $P_3$. Frangible portion 251, which when ruptured forms void or slit 247 transforming the now detached pouch margin 235 segment $P_3$ into handle structure 243. Again, as previously indicated, as segments $W_3$ and $P_3$ are substantially in alignment, waist margin frangible portion 249 and pouch margin frangible portion 251 are also corresponding. In an alternative embodiment (not shown), the frangible or perforated portions may be longitudinally positioned in spaced relation within the longitudinal distance L1, L2 spanned by waist margin 121 and pouch margin 135. In a further embodiment, not illustrated, the frangible or perforated portions may be "O" shaped, "X" shaped or any other shape which when ruptured is suitable for receiving at least one of a human finger, fingers or hand.

As a practical matter, when a user selects an absorbent article 101 in accordance with the embodiments disclosed herein pouch 127 lies flat against the rear portion 11 outer layer 107. Similarly, the handle structures 141, 143 are not deployed and the margins of both the pouch and the rear waist 135, 121 are adjacent to their respective structures. Said differently, the handle structures 141, 143 do not become readily apparent until a user actively deploys the handles 141, 143. Said still another way, when a user dons a new absorbent article 101 in accordance to the embodiments of the present invention, neither the extension of the absorbent article waist band 123, nor the act of pulling the absorbent article 101 over the user's lower body will interfere with the fit of the absorbent article 101 around a user's waist. The handles will not gap or cause discomfort.

In embodiments where the handles gap, the gap will not detract from the fit or comfort of the absorbent article because these portions are not convex and will not protrude.

Figure 23A:
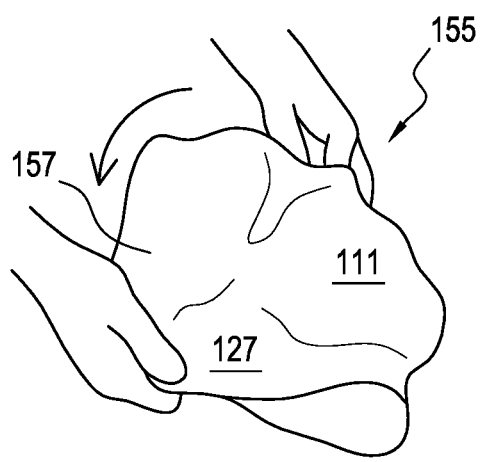
FIGS. 23A and 23B are perspective views of pouch inverted over soiled absorbent article.
Figure 23B:
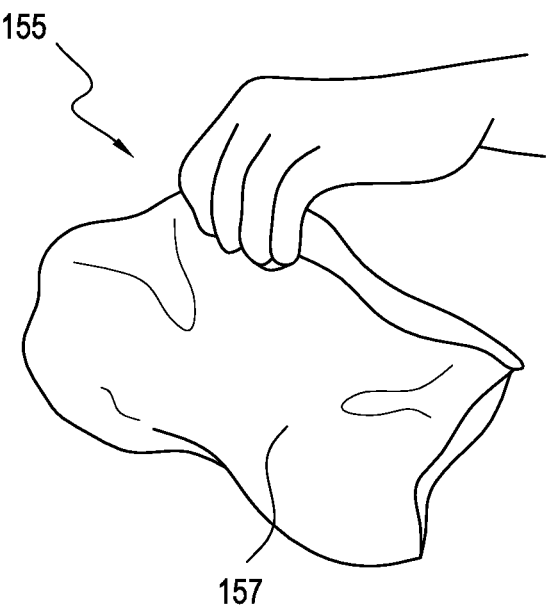
Figure 24:
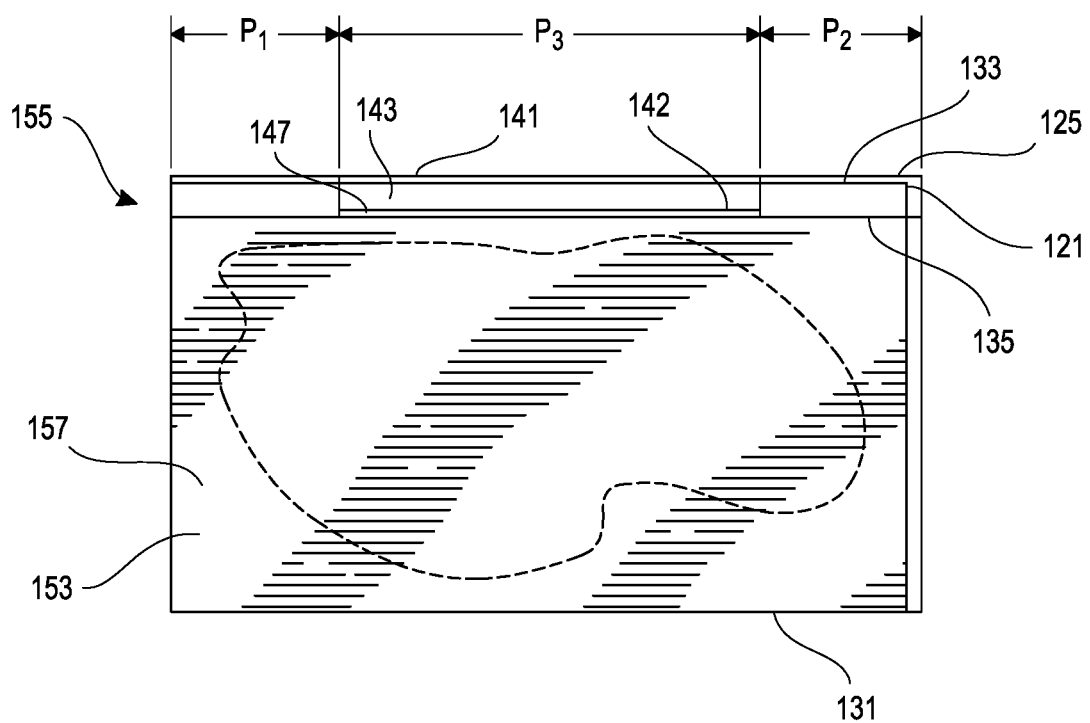
FIG. 24 is a plan view of the absorbent article of FIGS. 23A-23B.

As illustrated in FIGS. 23A and 23B, after doffing a used absorbent article 155, to conceal the absorbent article 155 within the pouch 127, the user breaks the seal 139 affixing the pouch opening 137 to the outer layer 107 of the absorbent article 155, reaches into pouch 127 and grasps the absorbent article 155 and draws it into the pouch 127. This action can be performed with one hand or in the alternative the user can use a second hand to hold the pouch 127 opening away from the absorbent article 155 to facilitate handling and inversion of the pouch 127 over the soiled absorbent article 155. Following inversion an inside surface 157 of pouch 127 is exposed to the environment. Said differently, front portion 109 of the soiled absorbent article 155 is now contained within inverted pouch 153 and rear portion 111 outer layer 107. Owing to the elastomeric properties of the pouch 127, the user does not need to roll, fold or otherwise needlessly manipulate the used absorbent article 155 other than to draw it into the inverted pouch 153. Such minimal handling will reduce the incident of accidental contact with biomatter contained within the absorbent article 155. Minimal handling reduces unpleasantness and improves sanitary conditions associated with disposal of a used absorbent article 155.

Figure 25:
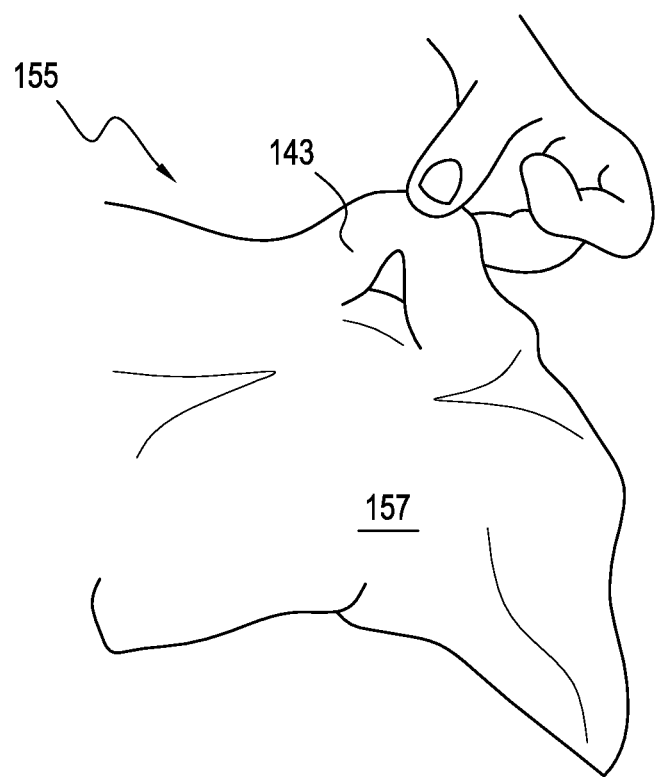
FIG. 25 is a perspective view of pouch inverted over soiled absorbent article with handles deployed.
Figure 26:
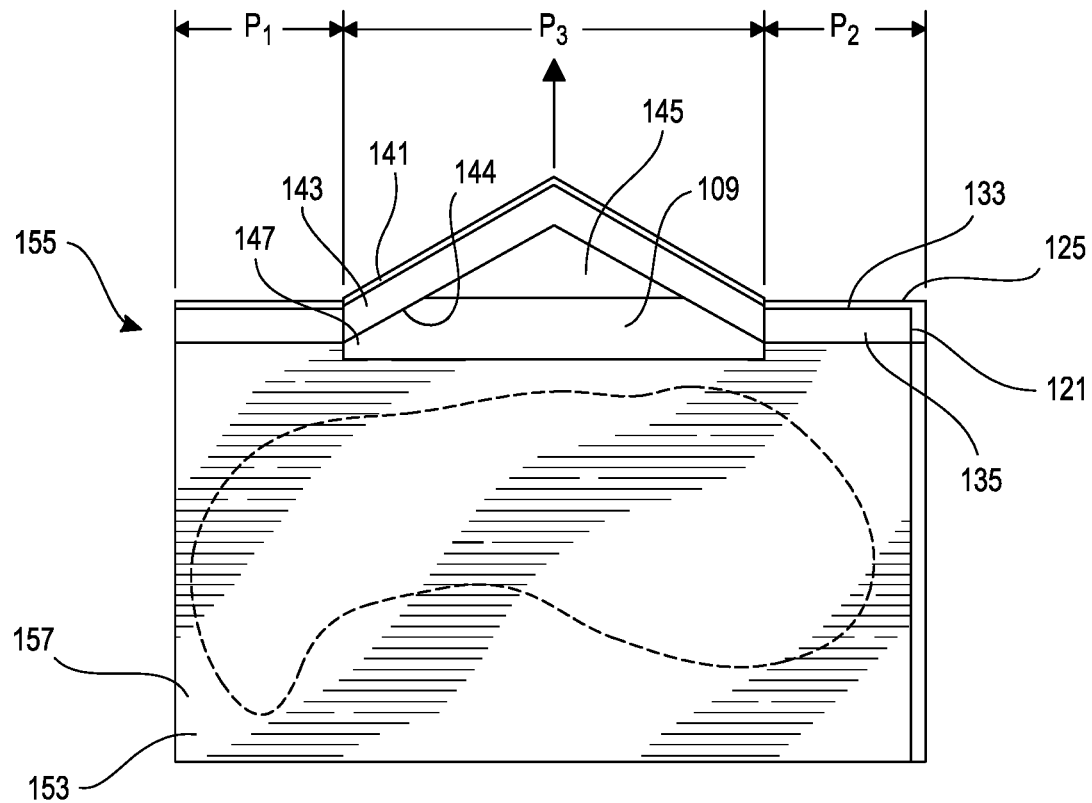
FIG. 26 is a plan view of the absorbent article of FIG. 25 with the handle structures in an open/deployed condition.

Once the used absorbent article 155 is concealed within the inverted pouch 153, the handles 143, 141 are deployed as illustrated by FIGS. 25 and 26. In a first embodiment (as earlier illustrated by FIGS. 13-15 and 18-20), a user inserts fingers or hands into voids 145, 147, gently grasps and extends handles 143, 141 and pulls them away from the absorbent article 155. In an alternative embodiment (as earlier illustrated by FIGS. 16-17A and 21-22A), a user ruptures the respective frangible portions 251, 249 of each of the pouch and waist margins 235, 221, inserts fingers or hands into newly formed voids 245, 247, gently grasps and extends handles 243, 241 and pulls them away from the absorbent article 255.

Owing to the elastomeric properties of the waist and pouch margins 121, 135, handles 141, 143 extend for easy transport of the concealed absorbent article 101. As previously discussed, segments $P_3$ and $W_3$ are substantially in alignment. Accordingly, each of the pouch margin void 147 and the rear waist margin void 145 will align after the pouch 127 is inverted 153 over a used absorbent article 155. The inverted pouch 153, together with the deployed handles 143, 141 forms a compact bag or pouch with a unified handle structure. The used absorbent article 155, concealed within the inverted pouch 153 can now be transported for disposal into an appropriate receptacle by grasping the aligned handle structures 143, 141. Owing to the compact nature of the disposal structure and any color indicia, a user's dignity can be maintained.

While the present invention has been described with reference to one or more particular embodiments, those skilled in the art will recognize that many changes may be made thereto without departing from the spirit and scope of the present invention. Furthermore, components from one embodiment can be used in other non-exclusive embodiments. Each of these embodiments and obvious various thereof is contemplated as falling within the spirit and scope of the invention, which is set forth in the following alternative embodiments.

What is claimed is:

1. An absorbent article comprising:
    a chassis comprising an outer layer, an absorbent layer and inner layer, wherein the chassis further comprises:
        a first portion,
        a second portion having a top edge,
        a waist margin extending along the second portion top edge, wherein a length of the waist margin is separated from the second portion top edge by a void extending along a section of the second portion top edge,
        a center portion extending between the first and second portions, and
        a plurality of side panels connected with the first portion and second portion, wherein the first portion, second portion and side panels form a waist opening and first and second leg openings; and
    an elastomeric pouch attached to the chassis second portion, the pouch having a margin extending along a top edge of the pouch, wherein a length of the pouch margin is separated from the pouch top edge by a void extending along a section of the pouch top edge;
    wherein the second portion waist margin void and the pouch margin void form first and second handles.

2. The absorbent article of claim 1, wherein the second portion void and pouch void are sized to receive at least one of a human finger, human fingers or a human hand.

3. The absorbent article of claim 1, wherein the second portion void is formed from a frangible segment of the second portion.

4. The absorbent article of claim 1, wherein the second portion void is formed by a slit cut in the second portion.

5. The absorbent article of claim 1, wherein the second portion void is formed by a perforated slit formed in the second portion, wherein the void is opened by tearing the second portion along the perforated slit.

6. The absorbent article of claim 1, wherein the pouch comprises first and second side walls, a bottom wall and an opening along a top portion of the pouch.

7. The absorbent article of claim 6, where in the pouch first and second side walls and bottom wall are attached to the second portion outer layer by at least one attachment device comprising one or more attachment devices selected from the group comprising: adhesive, thermal bonding, ultrasonic bonding, welding, embossing and stitching.

8. The absorbent article of claim 6, wherein the pouch first and second side walls and bottom wall are integral to the second portion outer layer.

9. The absorbent article of claim 6, wherein the pouch opening is releasably sealed to the second portion outer layer.

10. The absorbent article of claim 1, wherein when the pouch is inverted over the absorbent article, the pouch extends to encase the absorbent article.

11. The absorbent article of claim 1, wherein the first handle and the second handle are substantially in alignment.

12. The absorbent article of claim 1, wherein the first handle and the second handle extend longitudinally by substantially the same distance.

13. The absorbent article of claim 1, wherein the first handle and the second handle extend laterally by substantially the same distance.

14. The absorbent article of claim 1, wherein a center point of the first handle and a center point of the second handle are substantially aligned.

15. The absorbent article of claim 1, wherein the chassis outer layer and the pouch are constructed from the same material.

16. The absorbent article of claim 1, wherein the chassis outer layer and the pouch are constructed from different materials.

17. An absorbent article comprising:
a chassis comprising an outer layer, an absorbent layer and inner layer, wherein the chassis further comprises:
   a first portion,
   a second portion,
   a center portion extending between the first and second portions,
   a plurality of side panels wherein the first portion, second portion and side panels form a waist opening having a waist band, and first and second leg openings, and
   a waist margin substantially coextensive with the waist band, the waist margin comprising a first handle; and
a pouch, the pouch comprising a pouch margin, the pouch margin comprising a second handle.

18. The absorbent article of claim 17, wherein the pouch comprises an elastomeric material.

19. The absorbent article of claim 17, wherein the pouch is attached to an outer layer of the second portion.

* * * * *